(12) United States Patent
Albrecht et al.

(10) Patent No.: US 8,257,317 B2
(45) Date of Patent: *Sep. 4, 2012

(54) PLEATED TROCAR SHIELD

(75) Inventors: Jeremy J Albrecht, Rancho Santa Margarita, CA (US); Gary M. Johnson, Rancho Santa Margarita, CA (US); Donald L. Gadberry, Rancho Santa Margarita, CA (US); Henry Kahle, Rancho Santa Margarita, CA (US); Scott V. Taylor, Rancho Santa Margarita, CA (US); Kimball B. McGinley, Rancho Santa Margarita, CA (US)

(73) Assignee: Applied Medical Resources Corporation

( * ) Notice: Subject to any disclaimer, the term of this patent is extended or adjusted under 35 U.S.C. 154(b) by 0 days.

This patent is subject to a terminal disclaimer.

(21) Appl. No.: 13/165,931

(22) Filed: Jun. 22, 2011

(65) Prior Publication Data
US 2011/0251560 A1    Oct. 13, 2011

Related U.S. Application Data

(63) Continuation of application No. 12/685,541, filed on Jan. 11, 2010, now Pat. No. 7,988,671.

(60) Provisional application No. 61/143,497, filed on Jan. 9, 2009, provisional application No. 61/233,746, filed on Aug. 13, 2009.

(51) Int. Cl.
    *A61M 5/178* (2006.01)
(52) U.S. Cl. .................................. 604/167.06
(58) Field of Classification Search ............. 604/164.08, 604/167.01, 167.06
    See application file for complete search history.

(56) References Cited

U.S. PATENT DOCUMENTS 548,091 A    10/1895  Leidich
2,328,948 A *  9/1943  Bourke .................... 217/103
(Continued)

FOREIGN PATENT DOCUMENTS
EP         0051718 A1    5/1982
(Continued)

OTHER PUBLICATIONS

International Searching Authority/EP, International Search Report and Written Opinion of International Application No. PCT/US10/20663, dated Mar. 19, 2010, titled "Pleated Trocar Shield".

(Continued)

*Primary Examiner* — Christopher D Koharski
*Assistant Examiner* — Diva K Chander
(74) *Attorney, Agent, or Firm* — Patrick Y. Ikehara

(57) ABSTRACT

A surgical access device or trocar defines an access channel for instruments extending from a proximal end to the distal end thereof. The trocar comprises a cannula and a seal assembly disposed at the proximal end of the cannula. The seal assembly comprises a first or zero seal, a second or instrument seal, and a trocar shield disposed proximally of the first seal and the second seal. The first seal seals the access channel in the absence of an instrument extending therethrough. The second seal seals the access channel in the presence of an instrument extending therethrough. The trocar shield protects the first seal and second seal from damage as an instrument is advanced through the access channel. The trocar shield comprises an open proximal end and a tapered distal end comprising a plurality of longitudinal pleats, converging in an opening.

16 Claims, 17 Drawing Sheets

U.S. PATENT DOCUMENTS

| | | | |
|---|---|---|---|
| 3,197,173 A | | 7/1965 | Taubenheim |
| 4,240,411 A | | 12/1980 | Hosono |
| 4,424,833 A | | 1/1984 | Spector |
| 4,535,773 A | | 8/1985 | Yoon |
| 4,654,030 A | | 3/1987 | Moll |
| 4,655,752 A | * | 4/1987 | Honkanen et al. ............ 604/256 |
| 4,857,062 A | | 8/1989 | Russell |
| 4,895,346 A | | 1/1990 | Steigerwald |
| 4,909,798 A | | 3/1990 | Fleischhacker |
| 4,924,923 A | | 5/1990 | Boehmer |
| 4,929,235 A | | 5/1990 | Merry |
| 4,948,092 A | | 8/1990 | Kasper |
| 4,954,149 A | | 9/1990 | Fullemann |
| 4,960,412 A | | 10/1990 | Fink |
| 5,005,568 A | | 4/1991 | Loescher |
| 5,092,857 A | | 3/1992 | Fleischhacker |
| 5,098,393 A | | 3/1992 | Amplatz |
| 5,104,383 A | | 4/1992 | Shichman |
| 5,122,122 A | | 6/1992 | Allgood |
| 5,158,553 A | | 10/1992 | Berry et al. |
| 5,209,737 A | | 5/1993 | Ritchart |
| 5,304,143 A | | 4/1994 | Green |
| 5,308,336 A | | 5/1994 | Hart |
| 5,330,437 A | | 7/1994 | Durman |
| 5,342,315 A | | 8/1994 | Rowe |
| 5,385,553 A | | 1/1995 | Hart |
| 5,395,342 A | | 3/1995 | Yoon |
| 5,411,483 A | | 5/1995 | Loomas |
| 5,443,452 A | | 8/1995 | Hart et al. |
| 5,545,142 A | | 8/1996 | Stephens et al. |
| 5,603,702 A | | 2/1997 | Smith |
| 5,685,854 A | | 11/1997 | Green |
| 5,720,759 A | * | 2/1998 | Green et al. ................. 606/167 |
| 5,827,228 A | * | 10/1998 | Rowe ...................... 604/167.02 |
| 5,882,345 A | | 3/1999 | Yoon |
| 5,895,377 A | * | 4/1999 | Smith et al. ................... 604/256 |
| 5,906,595 A | | 5/1999 | Powell et al. |
| 6,569,120 B1 | * | 5/2003 | Green et al. ............. 604/167.04 |
| 7,083,626 B2 | | 8/2006 | Hart et al. |
| 7,597,701 B2 | * | 10/2009 | Hueil et al. .................... 606/185 |
| 7,717,878 B2 | * | 5/2010 | Smith ...................... 604/167.06 |
| 7,833,199 B2 | * | 11/2010 | Franer et al. ............. 604/167.03 |
| 7,988,671 B2 | * | 8/2011 | Albrecht et al. ......... 604/167.01 |
| 8,034,032 B2 | * | 10/2011 | Voegele et al. .......... 604/167.03 |
| 2005/0059934 A1 | * | 3/2005 | Wenchell et al. ........ 604/167.01 |
| 2005/0131349 A1 | * | 6/2005 | Albrecht et al. ......... 604/167.06 |
| 2005/0203467 A1 | | 9/2005 | O'Heeron et al. |
| 2005/0288634 A1 | * | 12/2005 | O'Heeron et al. ....... 604/167.06 |
| 2006/0211992 A1 | | 9/2006 | Prosek |
| 2006/0220325 A1 | * | 10/2006 | McFarlane .................... 277/607 |
| 2006/0253077 A1 | * | 11/2006 | Smith ...................... 604/167.06 |
| 2007/0051375 A1 | | 3/2007 | Milliman |
| 2007/0088277 A1 | * | 4/2007 | McGinley et al. ....... 604/167.01 |
| 2007/0255218 A1 | * | 11/2007 | Franer ...................... 604/167.02 |
| 2008/0132847 A1 | * | 6/2008 | Wing et al. .............. 604/167.05 |
| 2009/0005739 A1 | * | 1/2009 | Hart et al. ................ 604/167.06 |
| 2009/0240204 A1 | * | 9/2009 | Taylor et al. ............ 604/167.03 |
| 2010/0274193 A1 | * | 10/2010 | Patton et al. ............. 604/167.01 |

FOREIGN PATENT DOCUMENTS

| | | |
|---|---|---|
| EP | 0370720 A3 | 5/1990 |
| EP | 0420395 A2 | 4/1991 |
| EP | 1 759 645 | 3/2007 |
| WO | WO 2007/121425 | 10/2007 |
| WO | WO 2007121425 A1 * | 10/2007 |
| WO | WO 2009/117694 | 9/2009 |

OTHER PUBLICATIONS

The International Bureau of WIPO, International Preliminary Report on Patentability for Application No. PCT/US2010/020663, dated Jul. 12, 2011, titled "Pleated Trocar Shield".

US 5,803,626, 08/2006, Hart et al. (withdrawn)

* cited by examiner

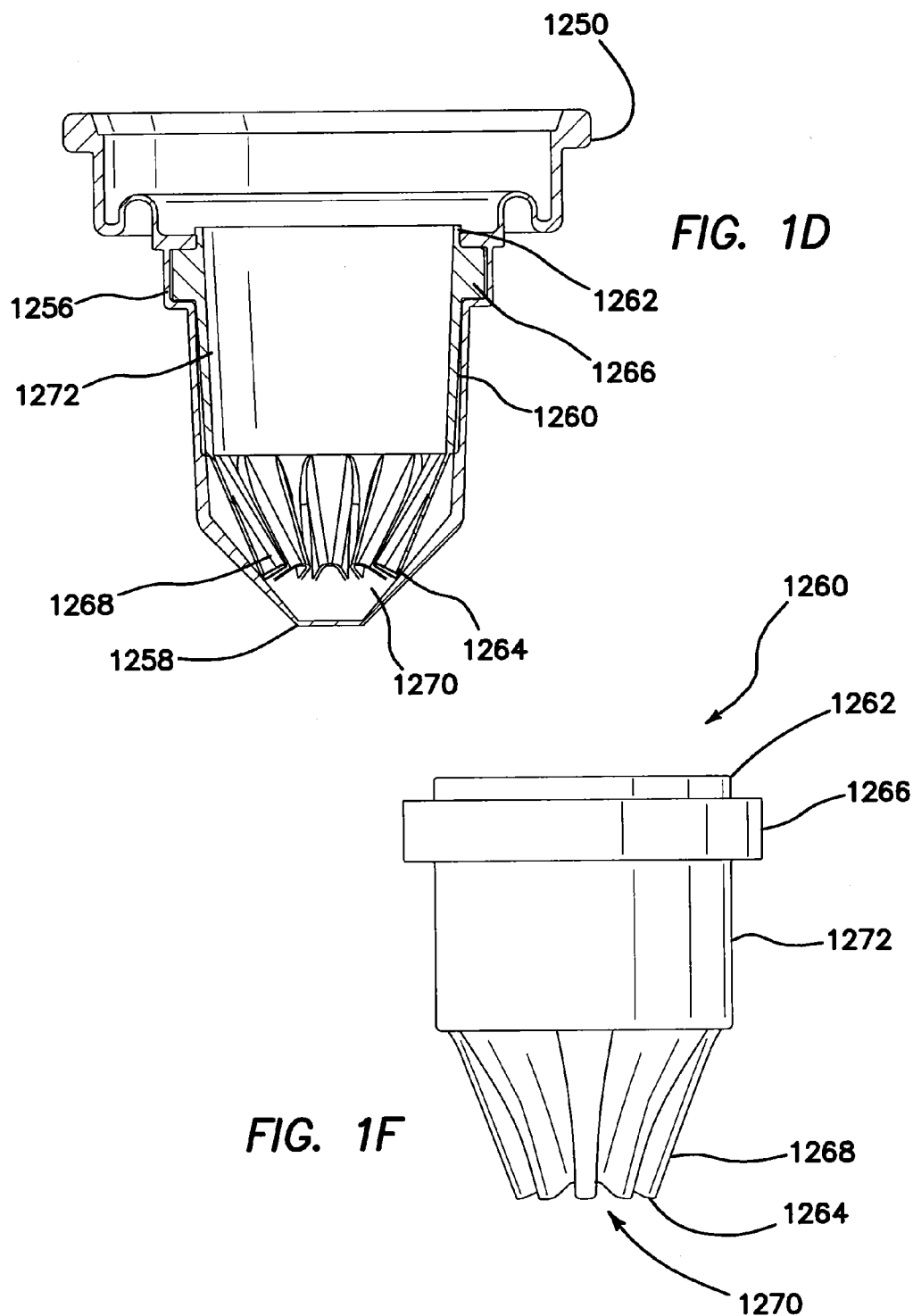

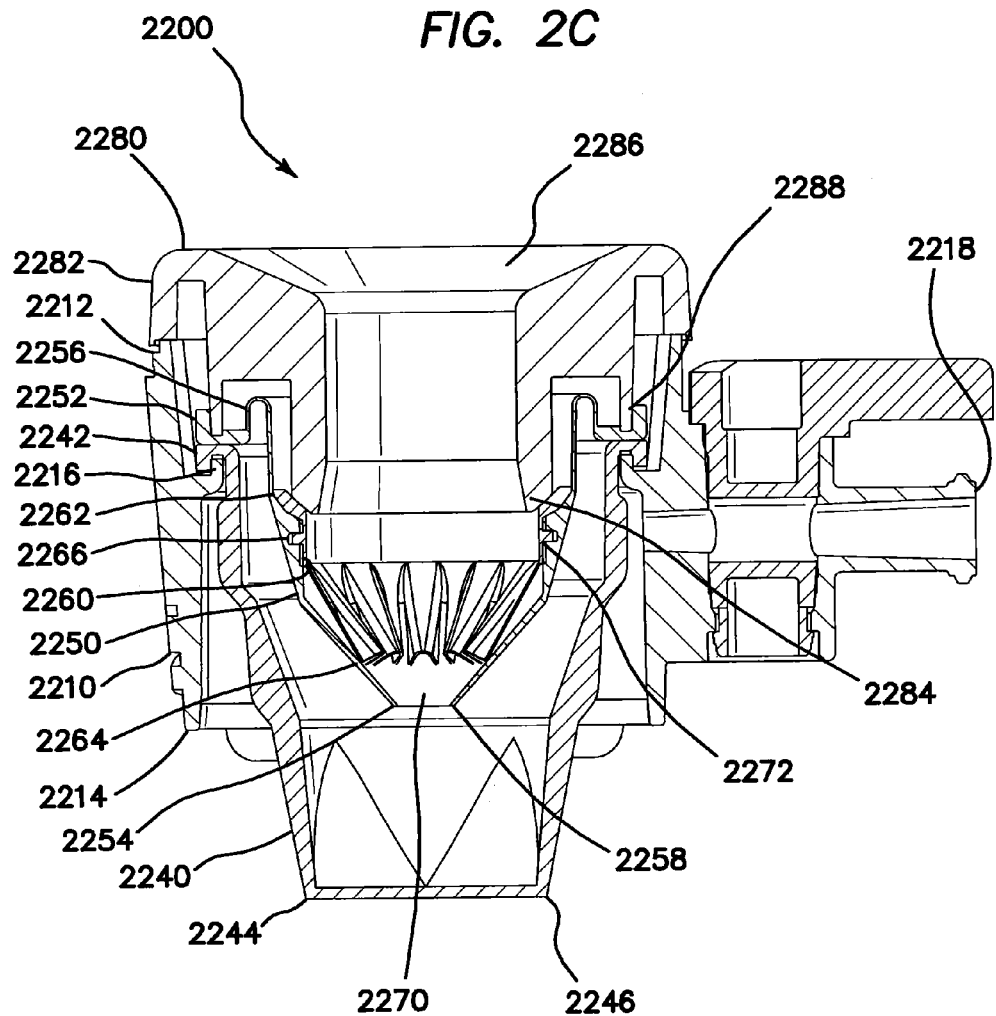

US 8,257,317 B2

PLEATED TROCAR SHIELD

CROSS-REFERENCE TO RELATED APPLICATION

This application is a continuation of U.S. application Ser. No. 12/685,541, filed Jan. 11, 2010, entitled "Pleated Trocar Shield" and claims the benefit of U.S. Application No. 61/143,497, filed Jan. 9, 2009, and U.S. Application No. 61/233,746, filed Aug. 13, 2009, the disclosures of which are incorporated by reference in their entireties.

BACKGROUND

1. Technical Field

This application is generally directed to surgical instruments, and more specifically to a surgical access device comprising a pleated shield.

2. Description of the Related Art

Laparoscopic surgery is a type of minimally invasive surgery in which instruments access internal structures of a patient's body through one or more access devices or trocars. In some laparoscopic procedures, a body cavity is inflated or insufflated with an insufflation gas, for example, carbon dioxide, which provides additional room for manipulating the instruments in the body cavity, thereby facilitating the surgical procedure. The term "pneumoperitoneum" refers to an abdominal cavity in an insufflated state. To maintain pneumoperitoneum, trocars are equipped with one or more seals that prevent insufflation gas from escaping as instruments are inserted, withdrawn, and/or manipulated during an operation. These seals typically comprise elastomeric materials, which can be damaged, particularly when instruments are inserted. Accordingly, trocars are often equipped with trocar shields that guide an instrument away from, or otherwise protect, vulnerable regions of the seals as the instrument is advanced through, withdrawn from, and/or manipulated within the trocar.

SUMMARY OF THE INVENTION

A surgical access device or trocar defines an access channel for instruments extending from a proximal end to the distal end thereof. The trocar comprises a cannula and a seal assembly disposed at the proximal end of the cannula. The seal assembly comprises a first or zero seal, a second or instrument seal, and a trocar shield disposed proximally of the first seal and the second seal. The first seal seals the access channel in the absence of an instrument extending therethrough. The second seal seals the access channel in the presence of an instrument extending therethrough. The trocar shield protects the first seal and second seal from damage as an instrument is advanced through the access channel. The trocar shield comprises an open proximal end and a tapered distal end comprising a plurality of longitudinal pleats, converging in an opening.

Some embodiments provide a surgical access device comprising: a longitudinal axis extending from a proximal end to a distal end, wherein the longitudinal axis defines an instrument access channel; a seal assembly comprising: a housing comprising a proximal end and a distal end; an instrument seal comprising a proximal end, a distal end, and an opening, wherein the instrument seal is disposed in the housing; and a seal shield comprising a frustoconical distal end converging to an opening, and a plurality of pleats extending proximally from the opening, wherein the plurality of pleats comprises a resilient material, unfolding the plurality of pleats expands the opening of the seal shield, and the seal shield is mounted to the instrument seal, wherein the opening in the instrument seal is aligned with the opening in the seal shield, and the instrument access channel extending through the opening in the instrument seal and the opening in the seal shield.

In some embodiments, the housing further comprises a cap closing the proximal end thereof, wherein the cap comprises a funnel-shaped entryway. In some embodiments, the cap secures the instrument seal to the housing. In some embodiments, a distal end of the funnel-shaped entryway defines a bearing surface against which the seal shield is pivotable.

In some embodiments, the instrument seal comprises a septum seal. In some embodiments, the proximal end of the instrument seal comprises a tubular first portion, the distal end of the instrument seal comprises a conical second portion that converges to the opening of the instrument seal, and the distal end of the seal shield nests in the conical second portion of the instrument seal.

In some embodiments, a portion of the seal shield defining the opening thereof comprises a non-elastomeric material. In some embodiments, the plurality of pleats of the seal shield comprises at least one of radial pleats and tangential pleats. In some embodiments, the plurality of pleats is helical. In some embodiments, the seal shield further comprises a stabilizing or retention member. In some embodiments, the stabilizing or retention member comprises a plurality of radially extending fins. In some embodiments, the seal shield further comprises a plurality of cams disposed on an interior surface proximal to the distal end thereof, wherein the cams define a funnel-shaped exitway.

In some embodiments, the seal shield is disposed at least one of proximal of the instrument seal and distal of the instrument seal.

In some embodiments, the seal shield is least one of mechanically and adhesively secured to the instrument seal. In some embodiments, at least one of the seal shield and the instrument seal comprises a radial flange that engages the other of the seal shield and the instrument seal.

In some embodiments, a smallest diameter of the opening of the seal shield is at least as large as a diameter of the instrument seal. In some embodiments, a smallest diameter of the opening of the seal shield is not larger than a diameter of the instrument seal. In some embodiments, the seal shield limits inversion of the instrument seal.

In some embodiments, the seal assembly further comprises a zero seal. Some embodiments further comprise a tubular cannula extending from the distal end of the housing.

Some embodiments provide a surgical access device comprising: a longitudinal axis defining an access channel through the access device from a proximal end to a distal end thereof; an elongate cannula comprising a proximal end and a distal end; and a sealing assembly disposed at the proximal end of the cannula, comprising: a zero seal sealing the access channel in the absence of an instrument extending therethrough; an instrument seal sealing the access channel in the presence of an instrument extending therethrough; and a trocar shield disposed proximally of the first and second seals in the sealing assembly, wherein the trocar shield comprises a open proximal end, and a convergent distal end comprising a plurality of longitudinal pleats, terminating in an opening, and wherein the trocar shield comprises a non-elastomeric material.

Some embodiments further comprise a cap securing the zero seal, the instrument seal, and the trocar shield in a seal housing, wherein the access channel extends through the cap, and wherein a distal end of the cap extends into and contacts the trocar shield. In some embodiments, the proximal end of the trocar shield is secured to the cap.

In some embodiments, the housing further comprises a gas inlet port.

In some embodiments, the proximal end of the trocar shield comprises a substantially cylindrical entry region. In some embodiments, the trocar shield comprises a plurality of stabilizing fins. In some embodiments, the trocar shield comprises a plurality of cams disposed on an inner surface thereof, wherein the cams define a funnel-shaped exitway.

In some embodiments, at least one of the instrument seal and the trocar shield comprises a radial flange that engages the other of the of the instrument seal and the trocar shield. In some embodiments, at least one of the instrument seal and the trocar shield comprises a groove that engages the radial flange.

In some embodiments, the surgical access device is a 5-mm trocar, a 11-12-mm trocar, or a 12-mm trocar.

Some embodiments provide a trocar comprising: a longitudinal axis defining an access channel through the trocar from a proximal end to a distal end thereof; an elongate cannula comprising a proximal end and a distal end; and a seal assembly disposed at the proximal end of the cannula. The seal assembly comprises: a first or zero seal sealing the access channel in the absence of an instrument extending therethrough; a second or instrument seal sealing the access channel in the presence of an instrument extending therethrough; and a tubular trocar shield disposed proximal to the first and second seals, wherein the trocar shield comprises a open proximal end, and a convergent distal end comprising a plurality of longitudinal pleats, terminating in an opening.

BRIEF DESCRIPTION OF THE DRAWINGS

FIG. 1D is a side cross section of an embodiment of a trocar shield and a second or instrument seal.

FIG. 1F is a side view of the pleated trocar shield illustrated in FIG. 1D.

FIG. 2C is a detailed longitudinal cross section of a seal assembly illustrated in FIG. 2B.

Similar reference numbers refer to similar components throughout.

DETAILED DESCRIPTION OF CERTAIN EMBODIMENTS

Figure 1A:
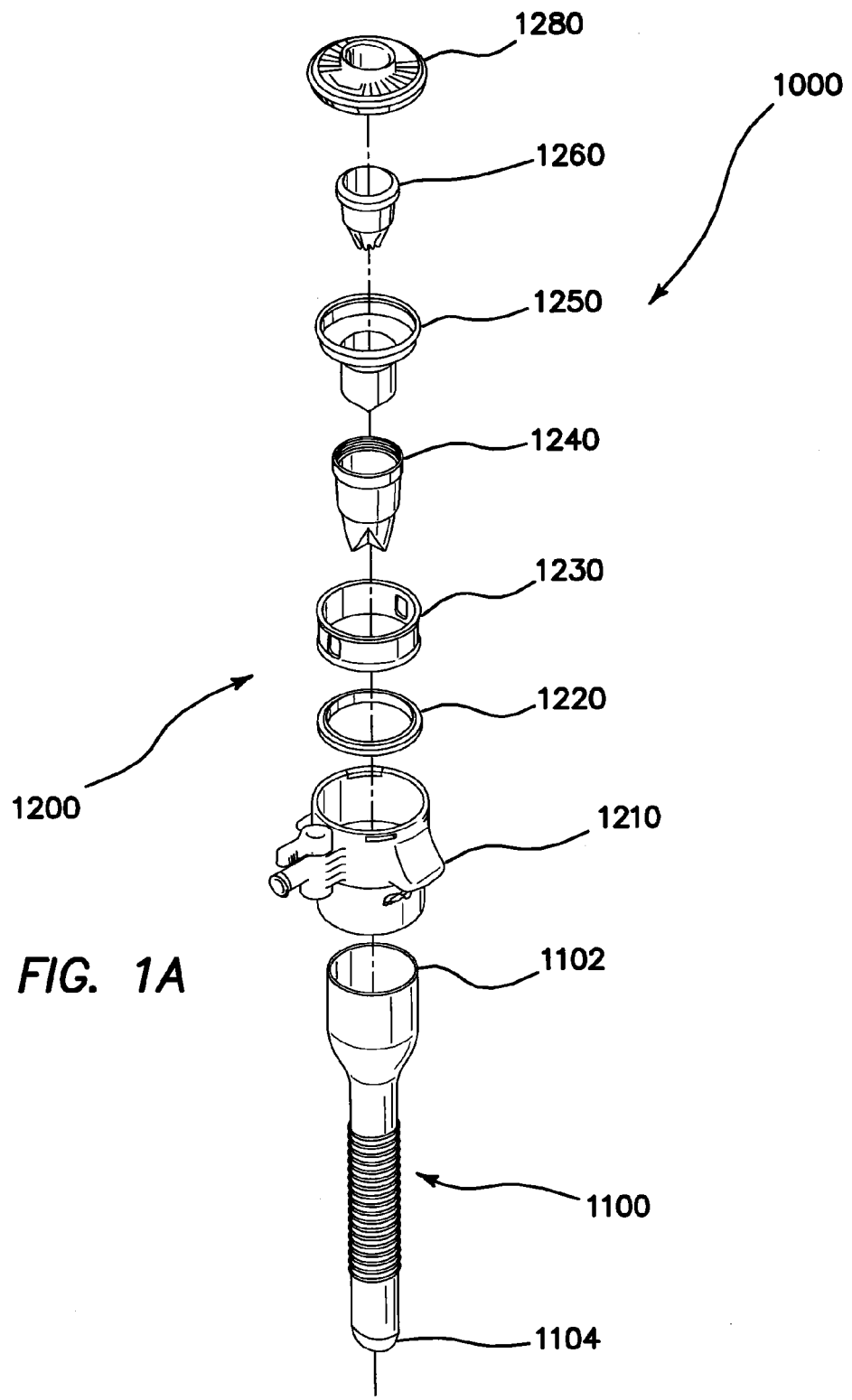
FIG. 1A is an exploded perspective view of an embodiment of a surgical access device comprising a pleated trocar shield.
Figure 1B:
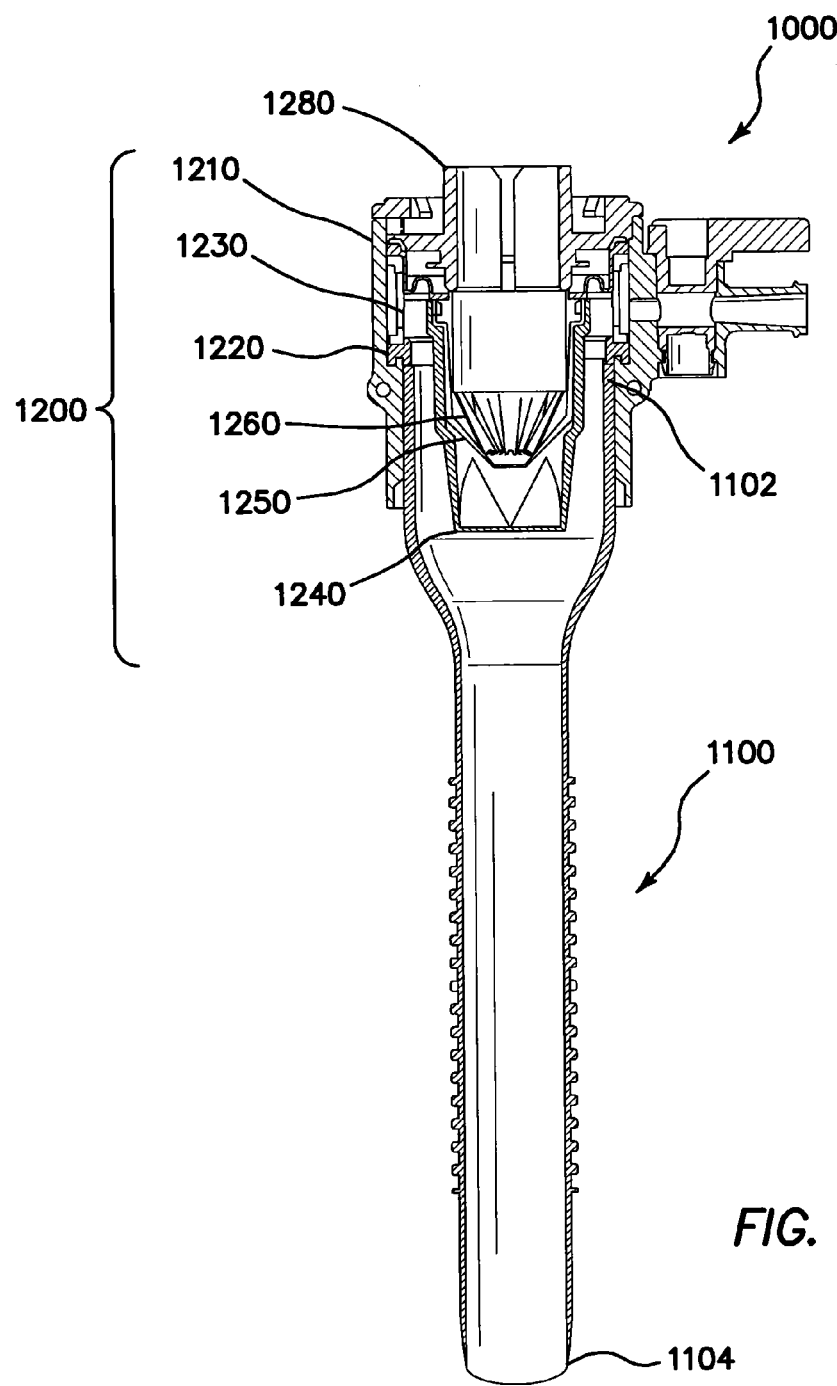
FIG. 1B is a longitudinal cross-sectional view of the trocar illustrated in FIG. 1A.

FIG. 1A is an exploded perspective view of an embodiment of a surgical access device or trocar 1000 comprising a pleated trocar shield. FIG. 1B is a longitudinal cross-sectional view of the access device 1000 illustrated in FIG. 1A. The access device 1000 comprises an elongate, hollow cannula 1100 comprising a longitudinal axis, a proximal end 1102, and a distal end 1104. The proximal end 1102 is dimensioned and configured for coupling to a seal assembly or trocar seal 1200, discussed in greater detail below. In the illustrated embodiment, the proximal end 1102 has a larger diameter, thereby defining a volume in which components of the seal assembly 1200 are disposed, as best seen in FIG. 1B. The cannula 1100 is dimensioned to accommodate a range of instruments, for example, instruments of predetermined diameters and/or lengths. The seal assembly 1200 comprises a longitudinal axis, which is generally coincident with the longitudinal axis of the cannula 1100, and which together, define an access channel through the trocar 1000. In some embodiments, the seal assembly 1200 is releasably secured to the cannula 1100.

The access device 1000 is typically manufactured in a range of sizes to accommodate instruments of different diameters, for example, up to about 5 mm, 8 mm, 11 mm, 12 mm, or 15 mm. Some embodiments of the access device 1000 accommodate a range of instrument sizes, for example, about 1 mm-5 mm, about 1 mm-16 mm, about 1 mm-25 mm, about 5 mm mm-15 mm, about 10 mm mm-12 mm, or about 10 mm mm-16 mm. Some embodiments are designed to accommodate a substantially single instrument size, for example, about 5 mm or about 10 mm. Embodiments of the access devices comprise cannula of different lengths. For example, some embodiments of the access device 1000 have working cannula lengths of about 55 mm, 75 mm, 100 mm, or 150 mm.

The cannula 1100 comprises any suitable material, for example, a biocompatible material. In some embodiments, the cannula 1100 comprises a polymer, for example, polycarbonate, polyvinyl chloride (PVC), polysulfone, polyamide, polyester, polyetheretherketone (PEEK), polyolefin, polyether block amide (PEBAX®), polyepoxide, polyurethane, polyacrylate, polyether, acrylonitrile-butadiene-styrene (ABS), polystyrene, blends, mixtures, copolymers, and the like. In some embodiments, the cannula 1100 comprises metal, glass, ceramic, and/or fiber. In some embodiments, the cannula 1100 comprises a composite, for example, comprising reinforcing fibers, a reinforcing structure, a layered structure, and the like. Some embodiments of the access device 1000 do not comprise a cannula.

Figure 1C:
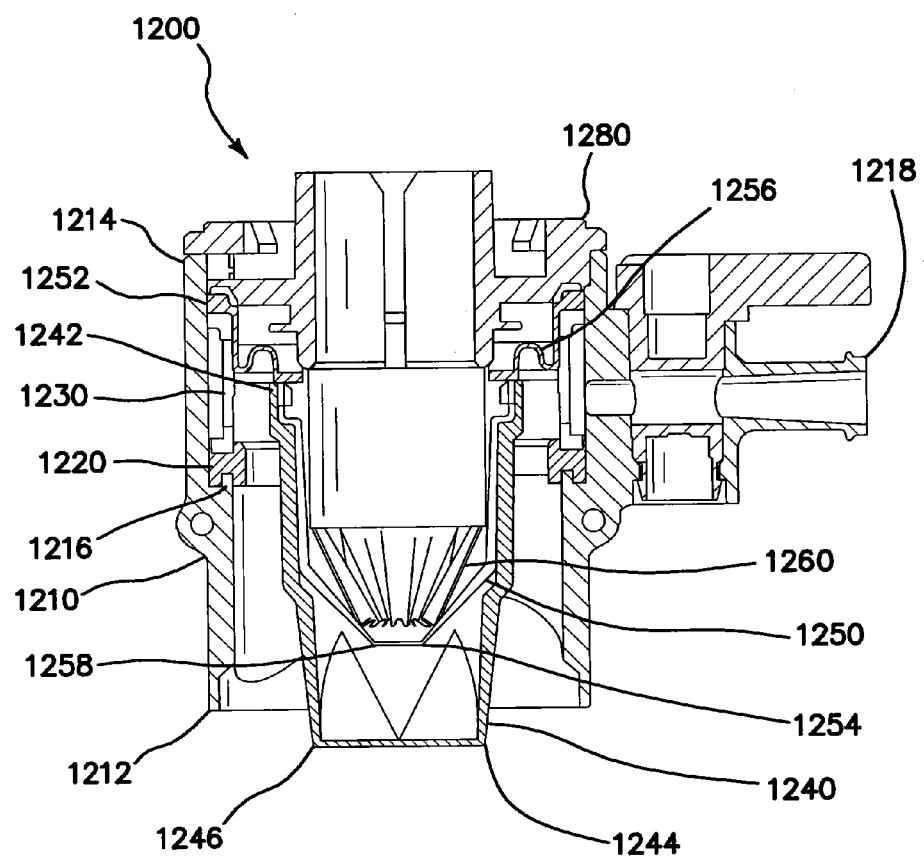
FIG. 1C is a detailed longitudinal cross section of a seal assembly illustrated in FIG. 1B.

The embodiment of the seal assembly or trocar seal 1200 comprises a housing 1210, a cannula seal 1220, a spacer 1230, a first or zero seal 1240, a second or instrument seal 1250, a trocar or seal shield 1260, and a cap 1280. The structure of the seal assembly 1200 is best seen in FIG. 1C, which is a longitudinal cross sectional of the trocar seal assembly illustrated in FIG. 1B.

In the illustrated embodiment, the housing 1210 comprises a generally hollow cylinder, open at both ends, and comprises a longitudinal axis, a distal end 1212, a proximal end 1214, an inner wall, and an outer wall. The proximal end 1214 is dimensioned to receive the cannula seal 1220, the spacer 1230, the first or zero seal 1240, the second or instrument seal 1250, and the trocar shield 1260 therethrough. A generally circular step or stop 1216 is disposed circumferentially on the inner wall of the housing 1210, which contacts and/or engages the cannula seal 1220. The cap 1280 engages the proximal end 1214 of the housing, thereby capturing the trocar shield 1260, the second or instrument seal 1250, the first or zero seal 1240, the spacer 1230, and the cannula seal 1220 between the cap 1280 and the stop 1216.

As best seen in FIG. 1B, the distal end 1212 of the housing is dimensioned to receive the proximal end 1102 of the cannula. In the illustrated embodiment, the proximal end 1102 of the cannula contacts the cannula seal 1220, thereby forming a gas-tight seal therebetween. Accordingly, in some embodiments, the cannula seal 1220 comprises a suitable elastomeric material, for example, rubber, synthetic rubber, silicone, ethylene propylene diene monomer (EPDM), ethylene-propylene copolymer (EP rubber), polyisoprene, polybutadiene, polyurethane, styrene-butadiene, ethylene vinyl acetate (EVA), polychloroprene (Neoprene®), perfluorelastomer (Kalrez®), and the like. As illustrated in FIG. 1B, portions of the first or zero seal 1240, the second or instrument seal 1250, and the trocar shield 1260 extend into the proximal end 1102 of the cannula.

In the illustrated embodiment, a gas inlet port 1218, comprising a valve, is disposed on the outer wall of the housing 1210, proximal of the step 1216. The gas inlet port 1218 fluidly connects the interior of the cannula 1100 with a source of gas, for example, an insufflation gas such as carbon dioxide. In the illustrated embodiment, the spacer 1230 comprises at least one opening 1232 (FIG. 1A) defining a fluid flow path between the gas inlet port 1218 and the hollow interior of the cannula 1100.

Some embodiments of the access device 1000 do not comprise a separate housing. Instead, the first seal, second seal, and trocar shield are disposed in the proximal end 1102 of the cannula. In these embodiments, the cannula 1100 and housing 1210 are integrated.

The first or zero seal 1240 forms a seal sufficient to maintain insufflation in the absence of an instrument extending therethrough, for example, comprising a single or double duckbill valve. In the illustrated embodiment, the first seal 1240 comprises a tubular member comprising a proximal end 1242 and a distal end 1244. The first seal 1240 is dimensioned to receive a portion of the second seal 1250 therein without interfering with the sealing functions thereof. The proximal end 1242 of the first seal is coupled to the second seal 1250 in the illustrated embodiment. Accordingly, the first seal 1240 and the second seal 1250 move and/or float as a unit. The distal end 1244 of the first seal comprises a double duckbill valve 1246 in the illustrated embodiment. Other types of valves known in the art are used in other embodiments. Some embodiments of the access device 1000 do not comprise a zero seal, for example, where the instrument seal 1250 also forms a zero seal, or where gas loss is not an issue.

The second or instrument seal 1250 forms a seal sufficient to maintain insufflation in the presence of an instrument extending therethrough. In the illustrated embodiment, the second or instrument seal 1250 comprises a tubular member comprising a proximal end 1252 and a distal end 1254. The proximal end 1252 comprises a bellows or convolution 1256 that extends radially toward the inner wall of the housing. The bellows 1256 is captured between the spacer 1230 and the cap 1280, thereby securing the second seal 1250 within the seal assembly. The distal end 1254 comprises a septum seal 1258 in the illustrated embodiment.

The first seal 1240 and the second seal 1250 each comprise a suitable elastomeric material. For example, in some embodiments, each of the first seal 1240 and the second seal 1250 independently comprises one or more of the cannula seal 1220 materials discussed above. In other embodiments, the second seal 1250 comprises an elastomeric gel material, for example, comprising an oil and a diblock and/or triblock copolymer comprising crystalline and amorphous blocks. Examples of suitable crystalline blocks comprise, for example, polystyrene. Examples of suitable amorphous blocks comprise, for example, at least one of polyethylene, polypropylene, hydrogenated polyisoprene, hydrogenated butadiene, and the like. Suitable oils include at least one of mineral oil, silicone oil, and fatty acid esters.

In the illustrated embodiment, the first seal 1240 is distal of the second seal 1250. In other embodiments, the first seal 1240 is proximal of the second seal.

Figure 1E:
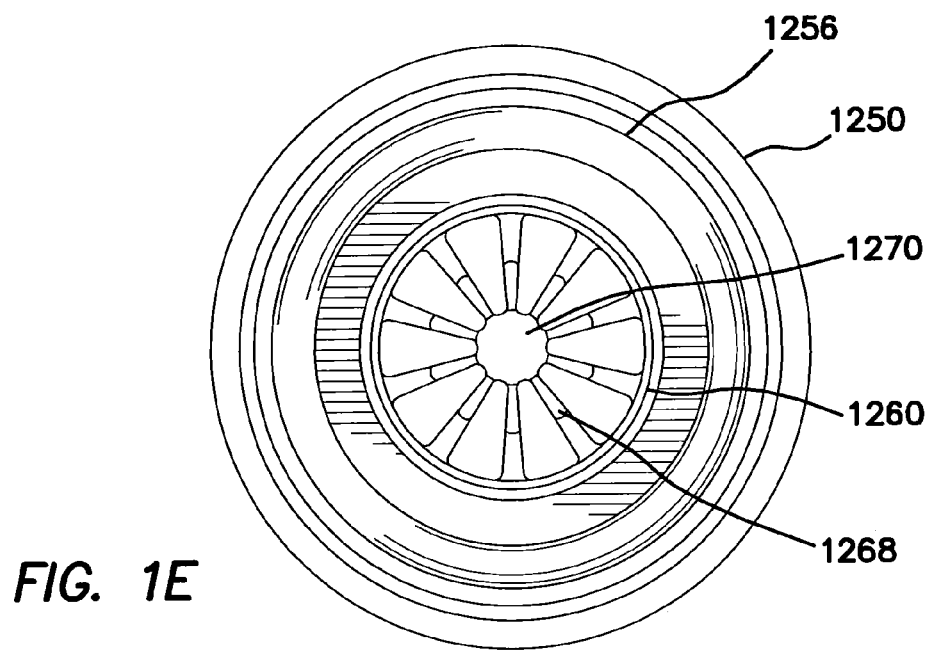
FIG. 1E is a top view of an embodiment of the trocar shield and the second seal illustrated in FIG. 1D.
Figure 1G:
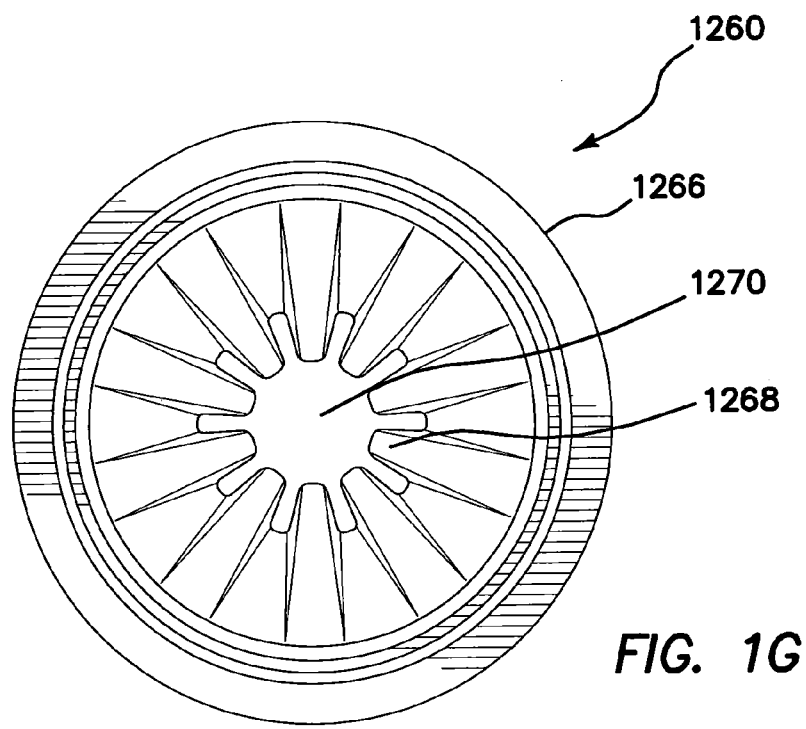
FIG. 1G is a top view of the pleated trocar shield illustrated in FIG. 1D.

FIG. 1D is a side cross section of an embodiment of the trocar shield 1260 and the second seal 1250. FIG. 1E is a top view of the trocar shield 1260 and the second seal 1250 illustrated in FIG. 1D. FIG. 1F a side view of the trocar shield 1260 illustrated in FIG. 1D, and FIG. 1G is a top view of the trocar shield 1260. In the embodiment illustrated in FIG. 1D, the trocar shield 1260 is generally tubular, comprising a proximal end 1262 and a distal end 1264. As best seen in FIG. 1D, the trocar shield 1260 is dimensioned and shaped to be received within, and consequently, carried on or mounted on, the second seal 1250 without interfering with the operation thereof. Consequently, the trocar shield 1260 moves or floats in concert with the second seal 1250. In the illustrated embodiment, the proximal end 1262 of the trocar shield comprises a radial flange 1266 that engages a corresponding recess 1256 in the second seal, thereby securing the trocar shield 1260 thereto. In some embodiments, the trocar shield 1260 is secured to the second seal 1250, using at least one of using an adhesive, welding, mechanical fastening, and the like, either in addition to, or instead of the flange 1266 and recess 1256 arrangement. The distal end 1264 is frustoconical, tapered, and/or funnel-shaped, dimensioned to fit or nest within the distal portion 1254 of the second seal. The frustoconical portion of the distal end 1264 comprises a plurality of convergent longitudinal pleats 1268, which are discussed in greater detail below, terminating in an opening 1270. A generally cylindrical entry region 1272 extends between the proximal end 1262 and the distal end 1264. In other embodiments, the entry region 1272 has another suitable shape, for example, frustoconical, an elliptical cross section, a polygonal prism, and/or pyramidal. Some embodiments do not comprise an entry region 1272.

The trocar shield 1260 comprises any suitable resilient material, for example, a polymer. Suitable polymers include polyolefins, polyethylene, polypropylene, polyvinyl chloride (PVC), polytetrafluoroethylene (PTFE), polyimide (Nylon®, Delrin®), copolymers, blends, mixtures, and the like. Some embodiments of the trocar shield 1260 comprise a spring metal, for example, 17-7 stainless steel. In some embodiments, the trocar shield 1260 comprises a composite. In some embodiments, the trocar shield 1260 is monolithic and/or integrally manufactured. In some embodiments, the trocar shield 1260 comprises a non-elastomeric material. For example, in some embodiments, at least the portion of the trocar shield 1260 surrounding or defining the opening 1270 comprises a non-elastomeric material. The non-elastomeric material reduces instrument drag compared with elastomeric materials, particularly on withdrawing instruments therethrough.

The trocar shield 1260 protects the second seal 1250 and the first seal 1240 from damage when an instrument is inserted through the access channel of the trocar 1000. Because embodiments of the second seal 1250 and/or the first seal 1240 comprise relatively soft materials, an instrument tip forced against such a material can tear and/or damage the material. If an instrument penetrates a wall of the second seal 1250, the instrument will likely contact a wall of the first seal 1240 as it is advanced, thereby increasing the likelihood of damage to the first seal 1240. The trocar shield 1260 directs an instrument towards the opening of septum seal 1258 disposed at the distal end 1254 of the second seal, and the zero seal 1246 disposed at the distal end 1244 of the first seal. For an instrument entering the proximal end 1262 of the trocar shield at an angle, the tip of the instrument contacts the entry region 1272. The entry region 1272 prevents the instrument tip from contacting the second seal 1250, and instead directs the tip towards the distal end 1264 of the trocar shield. The tip of an instrument entering the proximal end 1262 of the trocar shield off-axis will also contact the distal end 1264 of the trocar shield. In either case, the frustoconical shape of the distal end 1264 directs the instrument tip towards the opening 1270 as the instrument is advanced. Because the opening 1270 is aligned with and/or coaxial with the opening in the septum seal 1258 of the second seal and the center of the zero seal 1246 of the first seal, the trocar shield 1270 directs the tip of the instrument therethrough as the instrument is advanced, thereby reducing or minimizing damage to the second seal 1250 and the first seal 1240.

The pleats 1268 permit the opening 1270 at the distal end to expand and contract around an instrument as the instrument is advanced therethrough. In the illustrated embodiment, the pleats 1268 in their relaxed state define an opening 1270 with a smallest diameter similar in diameter or size, or smaller than the diameter or size of the opening in the septum seal 1258 disposed at the distal end 1254 of the second seal, thereby directing the tip of an instrument toward opening at the center of the septum seal 1258 and away from the elastomeric material of the second seal 1250. After the tip of the instrument clears the opening 1270 and septum seal 1258, the pleats 1268 permit the opening 1270 to expand as larger instruments are advanced therethrough. Accordingly, in some embodiments, the expanded circumference of the pleated portion of the distal end 1254 is at least as large as the circumference of largest instrument intended to be used in the trocar 1000, in particular, in embodiments in which the trocar shield 1260 comprises a generally non-compliant material. In some embodiments, the pleats 1268 comprise at least one of perforations, openings, and thinned and/or thickened portions at least some of the peaks and valleys thereof, thereby facilitating the folding and unfolding of the pleats 1268. In the illustrated embodiment, the peaks and valleys of the pleats 1268 are arcuate, which facilitates opening or unfolding the pleats, particularly to the maximum diameter or circumference. In other embodiments, at least one of the peaks and valleys is angular rather than arcuate.

In other embodiments, the smallest diameter of the opening 1270 of the trocar shield is at least as large as the diameter of the opening of the septum seal 1258. In some embodiments, the smallest diameter of the opening 1270 of the trocar shield is larger than the diameter of the opening of the septum seal 1258. The larger opening 1270 in some of these embodiments reduces instrument drag, particularly, in withdrawing instruments. For example, some instruments comprising irregular shapes and or projections are more easily withdrawn through a trocar shield 1260 with an opening 1270 as large as or larger than the opening of the septum seal 1258 compared with a trocar shield 1260 with an opening 1270 smaller than the opening of the septum seal 1258.

The number of pleats 1258 in the trocar shield depend on factors including the physical characteristics of the material from the trocar shield 1250 is fabricated, the thickness of the material, and the diameter of the largest instrument that the trocar shield 1250 is designed to accommodate, the relaxed diameter of the opening 1270, and the cone angle of the frustoconical portion. For example, a trocar shield 1250 with a larger cone angle typically comprises fewer pleats. Embodiments of the trocar shield 1250 comprise from about 3 to about 50 pleats, from about 5 to about 25 pleats, or from about 6 to about 20 pleats. In general, a trocar shield 1250 with a smaller diameter will have fewer pleats 1258. For example, embodiments of a trocar shield 1250 for a 5-mm trocar comprise from about 6 pleats to about 12 pleats. Embodiments of a trocar shield 1250 for a 12-mm trocar comprise from about 8 to about 16 pleats. Embodiments of a trocar shield 1250 for a 18-mm trocar comprise from about 10 to about 24 pleats.

In some embodiments, the trocar shield 1260 is fabricated in substantially the final shape. In other embodiments, the trocar shield 1260 is fabricated in another shape and assumes a final shape on assembly of the trocar 1000. For example, in some embodiments, the trocar shield 1260 is fabricated as a generally cylindrical tube comprising a proximal end 1262 and a distal end 1264. As the distal end 1264 of the trocar shield is urged against the frustoconical distal end 1254 of the second seal during assembly, the distal end 1264 naturally folds into a pleated configuration. In some embodiments, the proximal end 1262 of the cylindrical tube and the distal end 1264 of the cylindrical tube have different properties, for example, more rigid at the proximal end 1262 and more flexible at the distal end 1264. For example, in some embodiments, the proximal end 1262 comprises a plurality of layers of one or more polymer thin films, while the distal end 1264 comprises fewer layers, or even a single layer. The differences in flexibility facilitate the pleating process discussed above, and in some embodiments, permit the distal end 1264 or a portion thereof to invert as an instrument is withdrawn from the trocar 1000, while resisting or preventing inversion of the proximal portion 1262, thereby avoiding complete inversion of the trocar shield 1260. Inverting the distal end 1264 as the instrument is withdrawn reduces drag, hold-up, and/or snagging.

Some trocar shield designs for reducing seal damage include a frustoconical distal end comprising a plurality of flaps and/or petals separated by slots or similar openings. In some cases, the tip of an instrument can enter one of these slots and contact the material of second seal 1250, thereby increasing the likelihood of damage thereto. In contrast, the illustrated embodiment does not include slots or openings in the frustoconical portion, thereby reducing the likelihood of damage to the second seal 1250, as well as the first seal 1240. Furthermore, the contact area between the pleats 1268 and an instrument extending through the opening 1270 is smaller than the contact area for a similar trocar shield comprising flaps, thereby reducing friction and/or drag as the instrument is advanced or withdrawn.

The illustrated embodiment of the trocar shield 1260 reduces "cat-eye" leakage at the septum seal 1258, which occurs when lateral displacement an instrument extending therethrough stretches or distorts the opening in the septum seal, thereby creating an gap between the instrument and the septum seal opposite of the lateral displacement. Because the trocar shield 1260 is coupled to the second seal 1250, a lateral displacement of an instrument also displaces the trocar shield 1260, which urges the second seal 1250 in the same direction, thereby maintaining alignment between the opening 1270 and the septum seal 1258. Because the instrument, the opening 1270, and the septum seal 1258 move in concert, the incidence of cat-eye leakage is reduced.

Embodiments of the trocar shield 1260 also reduce the likelihood or probability of inverting the second seal 1250 as the instrument is withdrawn from the trocar 1000. In some embodiments, a portion of the trocar shield around the opening 1270 is invertible, which reduces instrument drag, hold-up, and/or snagging as the instrument is withdrawn.

In some embodiments of the seal assembly 1220, a distal pleated trocar shield (not illustrated) is disposed distally of the second seal 1250, either in addition to the trocar shield 1260 or instead of the trocar shield 1260. The distal end 1254 of the second seal is received within the distal trocar shield. In some of these embodiments, the distal trocar shield supports and/or acts as a backing to the second seal 1250, thereby reducing the likelihood of piercing or puncturing damage by an instrument tip during insertion. In some embodiments, the distal trocar shield protects the first seal 1240 from damage from instrument impingement. In some embodiments, the distal trocar shield reduces inversion of the first seal 1240.

In some embodiments, the distal trocar shield is coupled to the second seal 1250, as described above. In some of these embodiments, cat-eye leakage of the second seal 1250 is reduced, as discussed above. In other embodiments, the distal trocar shield is secured to the first seal 1240, for example, mechanically and/or adhesively. Examples of suitable mechanical securements include, for example, flange and groove, finger and notch, threads, bayonet mounts, mechanical fasteners, friction fit, and the like.

Some embodiments further comprise a protective thin film (not illustrated) disposed between the second seal 1250 and the trocar shield 1260, which provides additional protection to the second shield 1250 against mechanical damage. The protective film comprises any suitable material, for example, for example, a flexible polymer. In some embodiments, the protective film comprises at least one of polyamide, polyurethane, polyethylene, polyester, polyvinyl chloride, polyvinylidene chloride, PTFE, and the like.

Returning to FIG. 1C, the cap 1280 secures the cannula seal 1220, the spacer 1230, the first seal 1240, the second seal 1250, and the trocar shield 1260 in the housing 1210. The cap comprises a tubular entryway 1282 and a radial flange 1284 that contacts the bellows 1256 of the second seal, and that is secured to the proximal end 1214 of the housing. The entryway 1282 forms a portion of the access channel and is generally aligned with the longitudinal axis of the access device 1000.

Figure 2A:
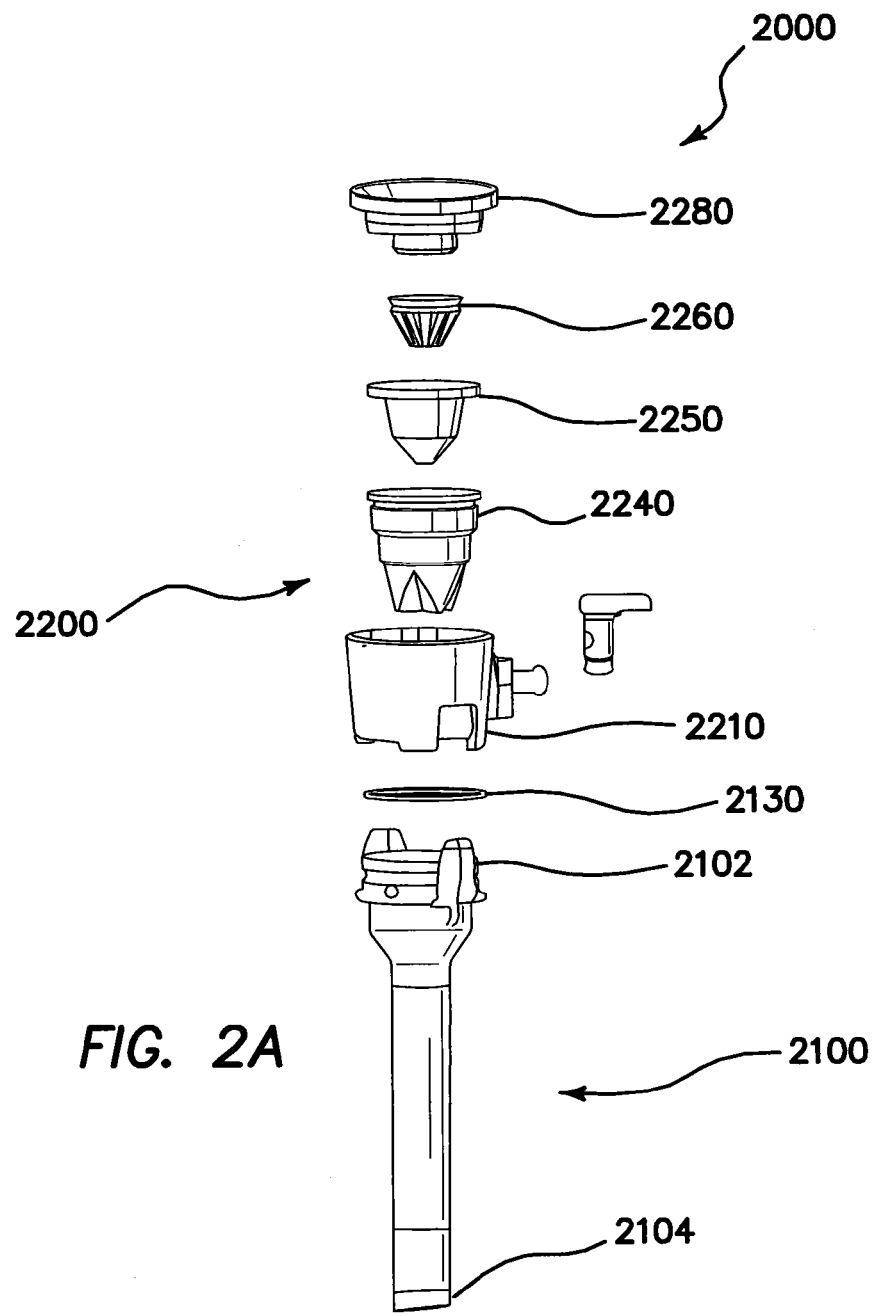
FIG. 2A is an exploded view of another embodiment of a surgical access device comprising a pleated trocar shield.
Figure 2B:
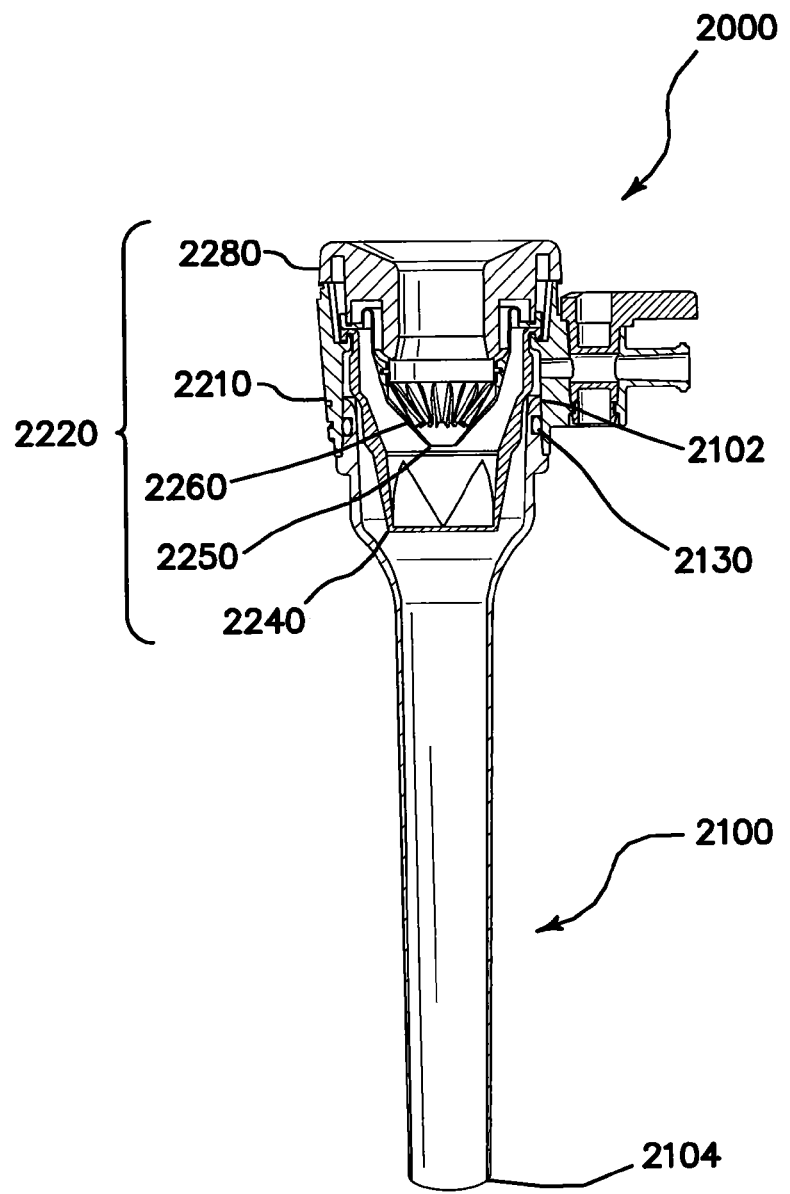
FIG. 2B is a longitudinal cross-sectional view of the trocar illustrated in FIG. 2A.

FIG. 2A is an exploded view of another embodiment of an access device 2000 comprising a pleated trocar shield. FIG. 2B is a longitudinal cross-sectional view of the access device 2000 illustrated in FIG. 2A. FIG. 2C is a detailed longitudinal cross section of a seal assembly illustrated in FIG. 2B. Because the embodiment illustrated in FIGS. 2A-2C is generally similar to the embodiment illustrated in FIGS. 1A-1C, suitable materials and dimensions are similar for both embodiments, unless otherwise specified.

The access device 2000 comprises a proximal end, a distal end, and a longitudinal axis defining an instrument access channel from the proximal end to the distal end. The access device 2000 comprises an elongate cannula 2100 disposed at the distal end and a seal assembly 2200 disposed at the proximal end. The cannula 2100 comprises a longitudinal axis, a proximal end 2102, a distal end 2104, and a cannula seal 2130 disposed at the proximal end of the cannula. In some embodiments, the cannula seal 2130 comprises an O-ring, for example. In the illustrated embodiment, the cannula 2100 is releasably coupled to the seal assembly 2200. As best seen in FIG. 2C, the seal assembly 2200 comprises a housing 2210, a first or zero seal 2240, a second or instrument seal 2250, a trocar shield 2260, and a cap 2280.

The housing 2210 comprises a longitudinal axis, a proximal end 2212, and a distal end 2214. A generally cylindrical body of the housing 2210 comprises an inner wall and an outer wall. The distal end 2214 is dimensioned to receive the proximal end 2102 of the cannula therein. As best seen in FIG. 2C, the cannula seal 2130 contacts the inner wall of the housing 2210, thereby forming a gas-tight seal between the cannula 2100 and the housing 2210.

The proximal end 2212 of the housing is dimensioned to receive the first or zero seal 2240, the second or instrument seal 2250, and the trocar shield 2260. The cap 2280 closes the proximal end 2212 of the housing. A generally circumferential stop or step 2216 is disposed on the inner wall of the housing 2210, which together with the cap 2280, captures and secures the first or zero seal 2240, the second or instrument seal 2250, and the trocar shield 2260 within the housing 2210. In the illustrated embodiment, the stop 2216 engages the first seal 2240, while the cap 2280 engages the second seal 2250. A gas inlet port 2218 is disposed on the outer wall of the housing 2210.

The first or zero seal 2240 comprises a longitudinal axis, a proximal end 2242, and a distal end 2244. The first seal 2240 is generally tubular in the illustrated embodiment and dimensioned to receive a portion of the second seal 2250 within the proximal end 2242 thereof. As discussed above, the proximal end 2242 of the first valve is dimensioned to engage the step 2216 of the housing. The distal end 2242 comprises a double duckbill valve 2246 in the illustrated embodiment, although those skilled in the art will understand that other types of valves are used in other embodiments, for example, a single duckbill valve, a flap valve, and the like.

The second or instrument seal 2250 comprises a longitudinal axis, a proximal end 2252, and a distal end 2254. The second seal 2250 is generally tubular, with a convolution or bellows 2256 extending generally radially outward at the proximal end 2252. The bellows 2256 extends towards the inner wall of the housing 2210 and provides a lateral degree of freedom or float to the second seal 2250, as well as a longitudinal degree of freedom. In the illustrated embodiment, the distal end 2254 of the second seal converges frustoconically, terminating in a septum seal 2258. In the illustrated embodiment, the portion of the bellows 2256 proximal to the housing 2210 is dimensioned to engage a portion of the cap 2280, as discussed in greater detail below.

Unlike the embodiment illustrated in FIGS. 1A-1C, the first seal 2240 is not coupled to the second seal 2250 in the illustrated embodiment. Consequently, the first seal 2240 and the second seal 2250 are free to move independently of each other. In the illustrated embodiment, the proximal end 2242 of the first seal contacts the proximal end 2252 of the second seal as best seen in FIG. 2C.

The pleated trocar shield 2260 in the illustrated embodiment comprises a longitudinal axis, a proximal end 2262 and a distal end 2264. The trocar shield 2260 is generally tubular and is received within the second seal 2250. The trocar shield 2260 comprises a radial flange 2266 that engages a corresponding recess in the second seal 2250, thereby securing the trocar shield 2260 thereto. Accordingly, the trocar shield 2260 and the second seal 2250 generally move in concert. The distal end 2264 of the trocar shield converges frustoconically, terminating in an opening 2270. The frustoconical portion comprises a plurality of longitudinal pleats 2268. A generally cylindrical entry region 2272 extends proximally from the frustoconical portion.

As discussed above, the cap 2280 is secured to the proximal end 2212 of the housing, thereby capturing the first seal 2240, the second seal 2250 and the trocar shield 2260 therebetween. In the illustrated embodiment, the cap 2280 comprises a longitudinal axis, a proximal end 2282, and the distal end 2284. The cap 2280 comprises a funnel-shaped entryway 2286 extending from a proximal end 2282 to the distal end 2284, which forms the proximal end of the access channel and guides instruments therethrough. The distal end 2284 of the entryway 2286 terminates adjacent to the proximal end 2262 of the trocar shield, thereby limiting longitudinal motion of the trocar shield 2260 and the second seal 2250 coupled thereto, towards the proximal end of the trocar 2000, thereby preventing inversion of the second seal 2260, for example, when an instrument is withdrawn from the trocar 2000. The proximal end 2282 of the cap extends radially from the entryway 2286. A circumferential portion of the proximal end 2282 is secured to the proximal end 2212 of the housing. A generally cylindrical flange 2288 contacts the proximal end 2252 of the second seal, thereby urging the second seal 2250 towards the stop 2216 of the housing.

Figure 3:
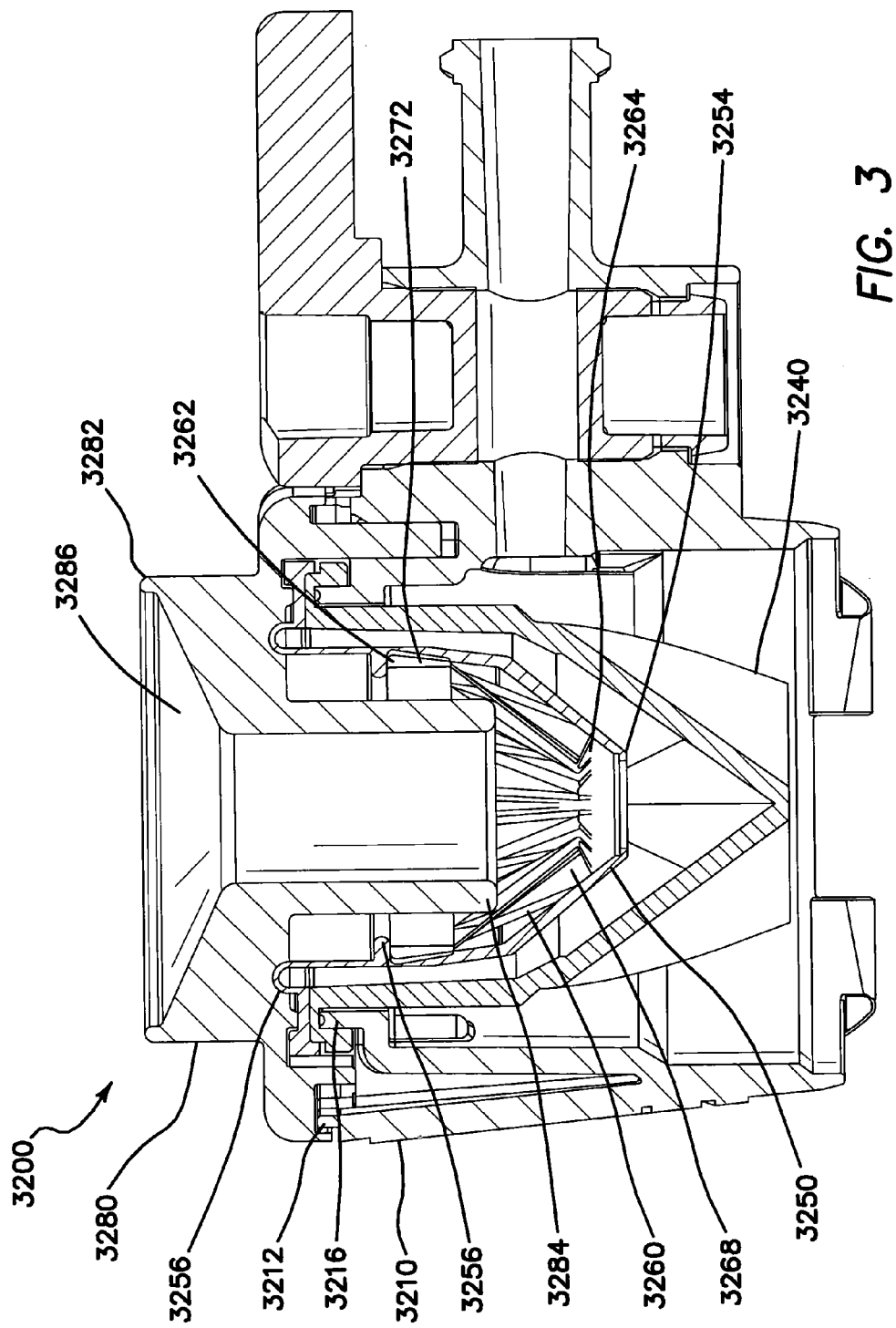
FIG. 3 is a side cross section of a seal assembly of another embodiment a surgical access device.

FIG. 3 is a side cross-sectional view of another embodiment of a seal assembly 3200 portion of an access device that is similar to the embodiments of the seal housing described above and illustrated in FIGS. 1A-2C. The seal housing 3200 is couplable with a cannula assembly as discussed above, thereby providing an access device. The seal assembly 3200 comprises a housing 3210 in which is disposed a first or zero seal 3240, a second or instrument seal 3250, and a pleated trocar shield 3260. In the illustrated embodiment, the zero seal 3240, instrument seal 3250, and trocar shield 3260 are secured within the housing 3210 between a circumferential stop or step 3216, disposed on an inner wall of the housing 3210, and a cap 3280 that closes a proximal end 3212 of the housing.

In the illustrated embodiment, the trocar shield 3260 is secured within the instrument seal 3250 between an inwardly extending radial flange 3256 of the instrument seal and a distal end 3254 of the instrument seal. A generally cylindrical entry region 3272 at a proximal end 3262 of the trocar shield contacts the flange 3256, while a distal end 3264 of the trocar shield contacts at or near the distal end 3254 of the instrument seal in the illustrated embodiment. Consequently, the trocar shield 3260 and instrument seal 3250 generally move in concert. In other embodiments, the trocar shield 3260 is coupled to the instrument seal 3250 in a different way, for example as in the embodiments illustrated in FIGS. 1A-2C and described above.

In the illustrated embodiment, the cap 3280 comprises a funnel-entry 3286 at a proximal end 3282 thereof, which defines a proximal end of an instrument access channel. The instrument channel extends longitudinally to a distal end 3284 of the cap, which extends into and contacts the trocar shield 3260, thereby defining a bearing surface against which the trocar shield 3260 pivots, for example, when accommodating off-axis movement of an instrument extending therethrough. In the illustrated embodiment, the distal end 3284 of the cap is generally cylindrical. In other embodiments, the distal end 3284 has a shape that facilitates its function as a bearing, for example, hemispherical or ball-shaped. In the illustrated embodiment, pleats 3268 on the trocar shield reduce a contact surface area between the trocar shield 3260 and the distal end 3284 of the cap, thereby reducing friction therebetween.

In some embodiments, contact between the distal end 3284 of the cap and the trocar shield 3260 provides an additional function, for example, reducing the likelihood of the trocar shield 3260 inverting, for example, when an instrument is withdrawn. Contact between the distal end 3284 of the cap and the trocar shield 3260 buttresses or reinforces the trocar shield 3260 as an instrument is withdrawn therefrom. As discussed above, embodiments of pleats 3268 on the trocar shield 3260 also reduce the likelihood of inversion. Because the trocar shield 3260 reduces the likelihood of the instrument seal 3250 inverting on instrument withdrawal, as discussed above, the illustrated embodiment also reduces the likelihood of instrument seal 3250 inversion.

Moreover, in some embodiments, the trocar shield 3260 is thinner than a similar trocar shield 3260 in which the trocar shield 3260 does not contact the cap 3280 because of the reinforcing or buttressing effect discussed above. Embodiments of a thinner trocar shield 3260 exhibit improved conformability to a range of instrument diameters, and/or accommodates larger instrument diameters, for example.

In the illustrated embodiment, the trocar shield 3260 contacts the distal end 3284 of the cap. A convolution or bellows 3256 at a proximal end 3252 of the instrument seal biases a distal end 3254 of the instrument seal towards the proximal end of the seal housing 3200. Because the trocar shield 3260 is carried in the distal end 3254 of the instrument seal, the trocar shield 3260 is also biased proximally, thereby urging the trocar shield 3260 against the distal end 3284 of the cap. Because the distal end 3254 of the instrument seal is displaceable distally along the instrument channel, in some situations, the trocar shield 3260 does not contact the distal end 3284 of the cap. For example, inserting an instrument through the seal assembly 3200 tends to urge the distal end 3254 of the instrument seal and trocar shield 3260 distally, thereby breaking the contact between the cap 3280 and the trocar shield 3260. Similarly, certain instrument manipulations will also break the contact therebetween. Under most other conditions, however, the trocar shield 3260 contacts the distal end 3284 of the cap, for example, with no instrument present, while withdrawing an instrument, and/or when manipulating an instrument off-axis.

In other embodiments, the trocar shield 3260 contacts the distal end 3284 of the cap only under certain conditions, for example, with no instrument present, while withdrawing an instrument, and/or when manipulating an instrument off-axis. In some of these embodiments, in a default condition, the trocar shield 3260 does not contact the cap 3280, for example, with no instrument inserted therein.

Figure 4A:
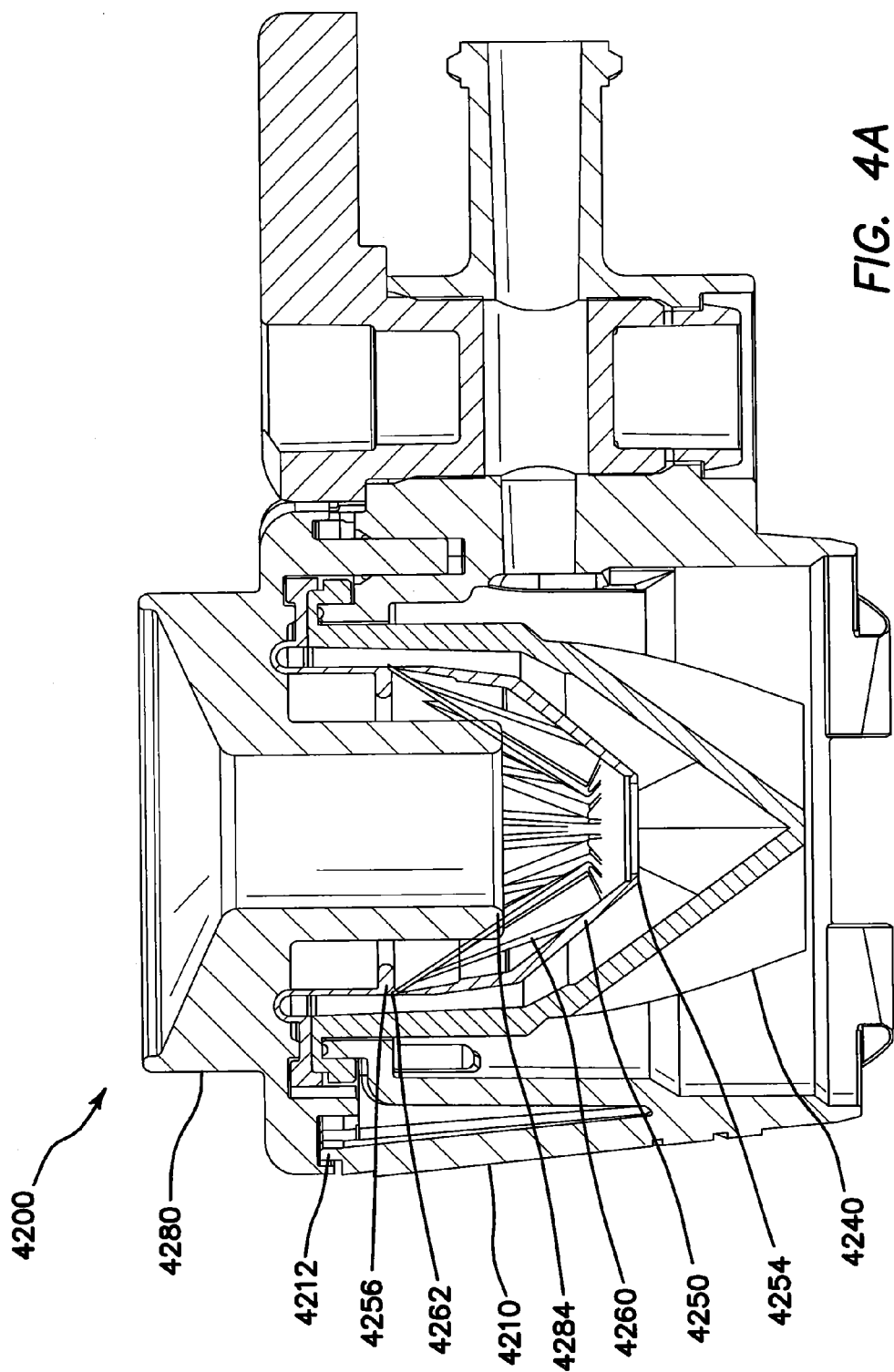
FIG. 4A is a side cross section of a seal assembly of another embodiment a surgical access device.

FIG. 4A is a side cross section of another embodiment of a seal assembly 4200 that is generally similar to the embodiment of the seal assembly 3200 illustrated in FIG. 3 and described above, as well as the embodiments illustrated in FIGS. 1A-2C and described above. The seal assembly 4200 comprises a seal housing 4210 in which are disposed a first or zero seal 4240, a second or instrument seal 4250, and a trocar shield 4260. A cap 4280 closes a proximal end 4212 of the seal housing and secures the zero seal 4240, the instrument seal 4250, and the trocar shield 4260 therein. In the illustrated embodiment, the seal housing 4210, zero seal 4240, and instrument seal 4250 are generally similar to the corresponding components of the embodiment 3200 illustrated in FIG. 3 and described above.

Figure 4B:
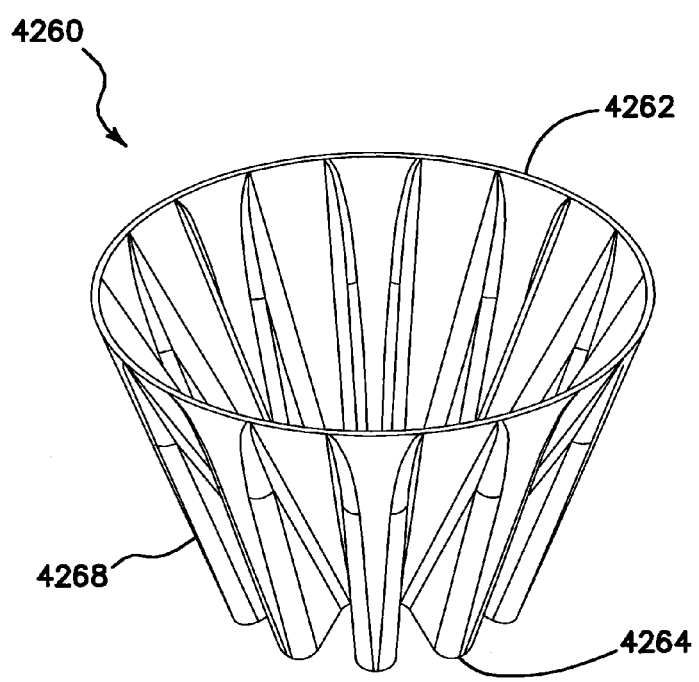
FIG. 4B is a perspective view of a trocar shield of the embodiment illustrated in FIG. 4A.

As best seen in FIG. 4B, which is a perspective view of the trocar shield 4260, the trocar shield 4260 is generally frustoconical, open at a proximal end 4262 and distal end 4264, and comprises a plurality of longitudinal pleats 4268. The trocar shield 4260 is generally similar to the embodiments illustrated in FIGS. 1A-1F, 2A-2C, and 3 and described above, except that the proximal end 4262 of the trocar shield does not comprise a generally cylindrical entry region. Compared with the embodiment illustrated in FIG. 3, embodiments of trocar shields not comprising the entry region exhibit greater compliance at the proximal end, thereby facilitating expanding the pleats when an instrument is inserted therethrough.

Returning to FIG. 4A, the trocar shield 4260 in the illustrated embodiment is coupled to the instrument seal 4250 between a inwardly extending radial flange or lip 4256 on the instrument seal and a distal end 4254 of the instrument seal, which is similar to the arrangement illustrated in FIG. 3. A distal end 4284 of the cap extends through the proximal end 4262 of the trocar shield and contacts an inner surface thereof. As with the embodiment illustrated in FIG. 3, the distal end 4284 of the cap serves as a bearing on which the trocar shield pivots or pendulates, for example, when pivoting an instrument extending through the seal housing 4200. Those skilled in the art will understand that the embodiment of the trocar shield 4260 illustrated in FIGS. 4A and 4B is also useful in the embodiments of the access device illustrated in FIGS. 1A-2C.

Figure 5A:
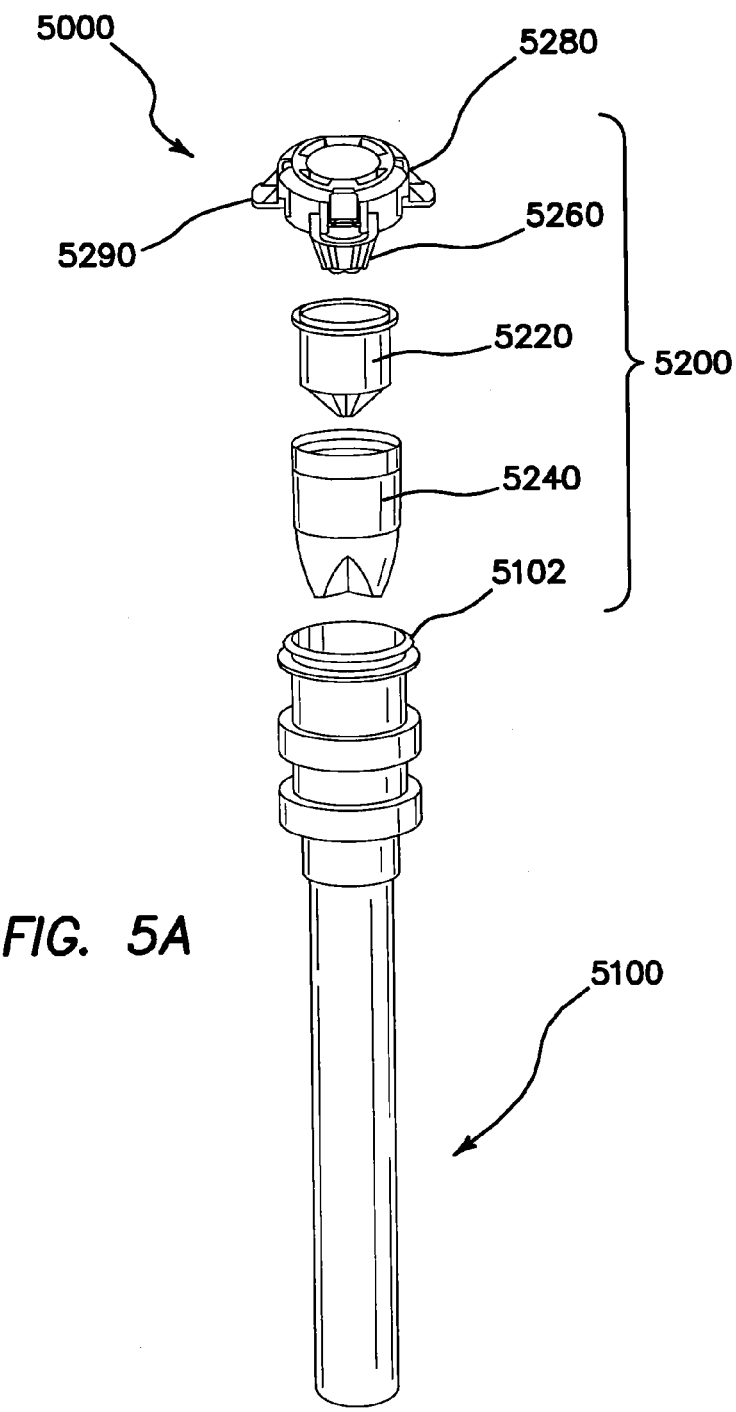
FIG. 5A is an exploded view of another embodiment of a surgical access device.

FIG. 5A is an exploded view of another embodiment of a trocar or surgical access device 5000 comprising a cannula 5100 and a seal assembly 5200 that is generally similar to the embodiments described above.

Figure 5B:
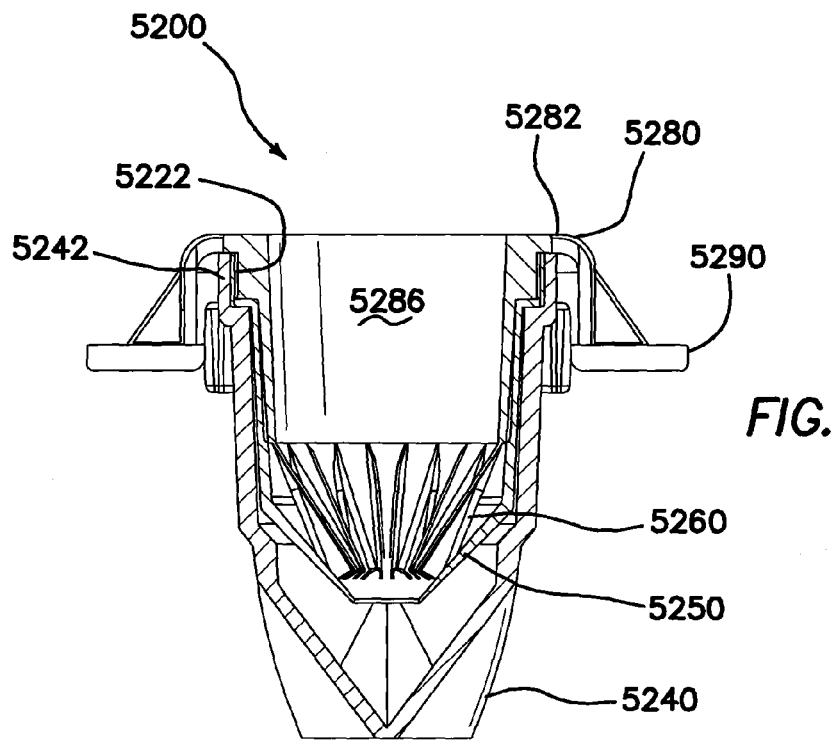
FIG. 5B is a side cross section of a seal assembly of the surgical access device illustrated in FIG. 5A.

FIG. 5B is a side cross section the seal assembly 5200, which is simplified compared with the embodiments described above, comprising fewer components. The seal assembly 5200 comprises a first or zero seal 5240, a second or instrument seal 5250, a trocar shield 5260, and a cap 5280.

Figure 5C:
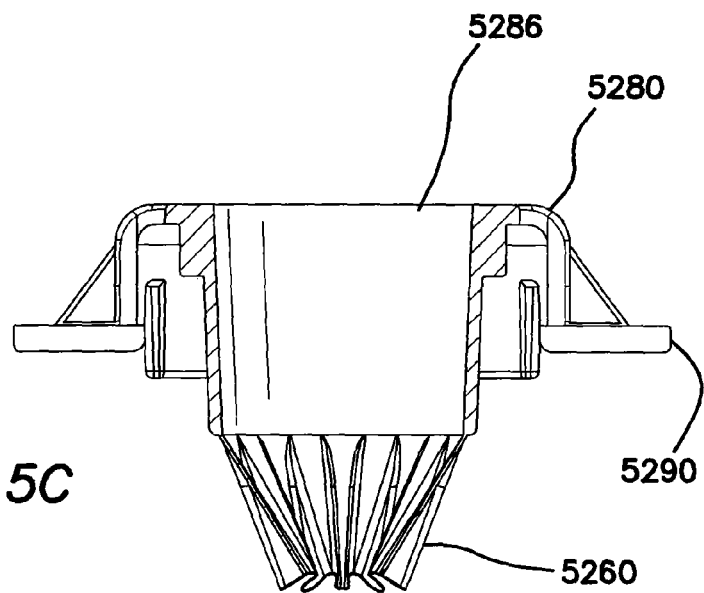
FIG. 5C is a side cross section of a cap and trocar shield of the seal assembly illustrated in FIG. 5B.

A proximal end 5262 of the trocar shield 5260 is secured to an entry funnel 5286 of the cap 5280, as best seen in FIG. 5C, which is a side cross section of the trocar shield 5260 and cap 5280. Consequently, in some embodiments, the trocar shield 5260 does not pendulate and/or float. In other embodiments, the entry funnel 5286 comprises a flexible material, thereby endowing the trocar shield 5260 a degree of float. In some embodiments, the trocar shield 5260 and cap 5280 are integrated, unitary, and/or monolithic. In other embodiments, the trocar shield 5260 and cap 5280 are separately manufactured and subsequently coupled.

Returning to FIG. 5B, the first or zero seal 5240, the second or instrument seal 5250 are generally similar to the embodiments described above. A proximal end 5242 of the first seal and a proximal end 5252 of the second seal are secured to a portion of a proximal end 5282 of the cap in the illustrated embodiment. In some embodiments, the proximal end 5242 of the first seal and the proximal end 5252 of the second seal are coupled, for example, adhesively. In some embodiments, at least one of the proximal end 5242 of the first seal and the proximal end 5252 of the second seal is secured to the cap 5280, for example, adhesively and/or mechanically. When the seal assembly 5200 is coupled with the cannula 5100, the proximal end 5242 of the first seal and the proximal end 5252 of the second seal are captured between the cap 5280 and a proximal end 5102 (FIG. 5A) of the cannula 5100, thereby securing the first seal 5240 and the second seal 5250 therebetween.

As illustrated in FIGS. 5A and 5B, the cap 5280 comprises a plurality of snaps 5290 that releasably engage a corresponding flange 5110 (FIG. 5A) at the proximal end 5102 of the cannula, thereby securing the cannula 5100 to the seal assembly 5200. In the illustrated embodiment, the snaps 5280 are manually disengageable, thereby permitting tool-free assembly and disassembly of the cannula 5100 from the seal assembly 5200, for example, when retrieving a specimen through the cannula 5100 or for rapid de-insufflation. Similar access devices are disclosed in U.S. application Ser. No. 11/677,994, filed Feb. 22, 2007, the disclosure of which is incorporated by reference in its entirety.

Figure 6A:
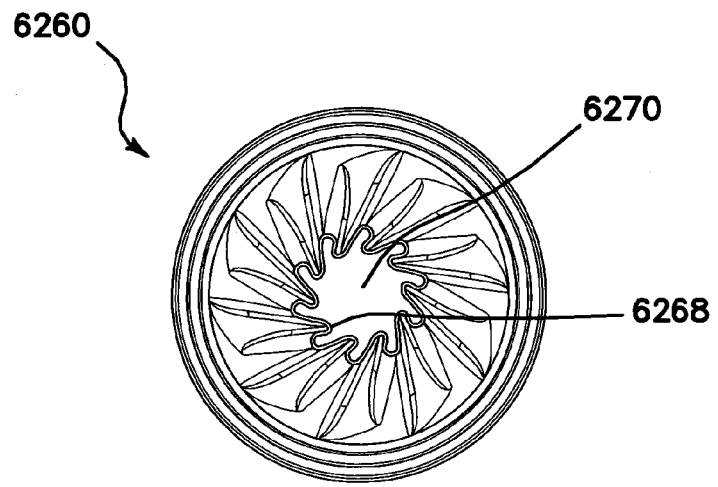
FIG. 6A is a top view and FIG. 6B is a side view of another embodiment of a pleated trocar shield.
Figure 6B:
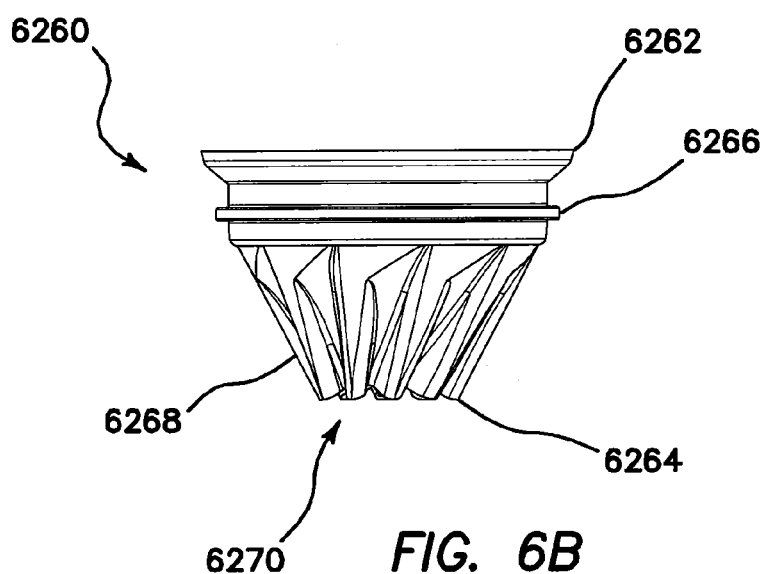

FIG. 6A is a top view, and FIG. 6B is a side view of another embodiment of a trocar shield 6260, which is generally similar to the embodiments discussed above, and which is useful in the access devices discussed above. The trocar shield 6260 comprises a proximal end 6262 and a distal end 6264. The distal end 6264 is generally frustoconical, converging to an opening 6270. A radial flange 6266 disposed at or near the proximal end 6262 engages a matching groove in an instrument seal, for example, as illustrated in FIG. 1D and described above, thereby securing the trocar shield 6260 to the instrument seal.

A plurality of pleats 6268 extend generally proximally from the opening 6270. The pleats 6268 are similar to the embodiments discussed above, except that each pleat 6268 is angled or tilted such that the axes of the pleats 6268 are non-radial, that is, the peaks and valleys of the pleats 6268 angled from radial axes of the trocar shield 6260, as best seen in FIG. 6A. In the illustrated embodiment, peaks of the pleats 6268 are all angled in a counterclockwise direction. Other embodiments comprise pleats 6268 that are angled in a clockwise direction, or angled in both directions.

As a consequence of the angling or tilting, a smallest diameter of the opening 6270 is not defined by the tips of the peaks, but instead, defined by portions of the peaks adjacent to the tips of the peaks, and/or straight portions of the pleats 6268 extending between the peaks and valleys. Such pleats are referred to as tangential pleats herein. In contrast, pleats in which the axes of the pleats are radial, as illustrated, for example, in FIGS. 1A-5C are referred to herein as radial pleats. In some embodiments, a trocar shield comprising tangential pleats exhibits reduced drag on instrument insertion and withdrawal compared with a similar trocar shield comprising radial pleats. Angling the axis of a pleat such that an instrument does not contact the tip of the pleat defines a lever arm that facilitates further angling or tilting of the pleat, thereby enlarging the opening 6270.

Returning to FIGS. 6A and 6B, the pleats 6268 are also helical. In the illustrated embodiment, the helices are right-handed. In other embodiment, the pleats 6268 are left-handed helices, or are not helical.

Figure 7A:
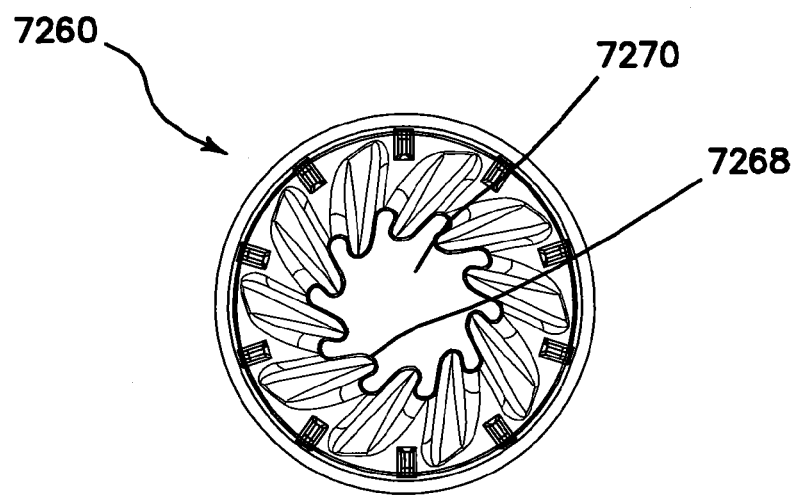
FIGS. 7A and 7B are top and side views of another embodiment of a trocar shield.
Figure 7B:
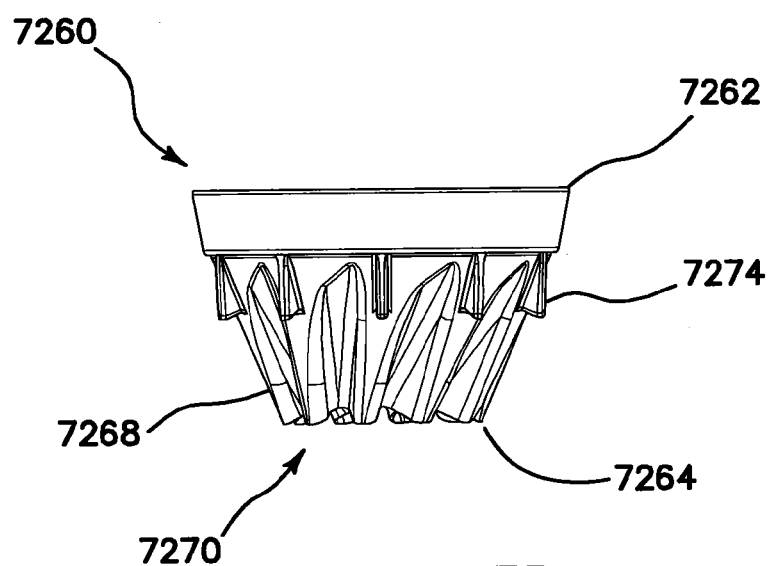

FIGS. 7A and 7B are top and side views of another embodiment of a trocar shield 7260 that is generally similar to the embodiments described above, and that is useful in the access devices discussed above. The trocar shield 7260 is generally frustoconical, comprising a wider proximal end 7262 that tapers to a narrower distal end 7264. The distal end 7264 terminates in an opening 7270. A plurality of tangential pleats 7268 extend generally proximally from the distal end 7264. The trocar shield 7260 also comprises a retention or stabilizing member, which in the illustrated embodiment, comprises a plurality of radially extending retention or stabilizing fins 7274 disposed between the pleats 7268 towards the proximal end 7262 of the trocar shield. The illustrated embodiment comprises a fin 7274 disposed between every pair of pleats 7268. Other embodiments comprise more or fewer fins 7274. In some embodiments, the number and/or spacing of the fins 7274 are not critical. In other embodiments, the retention or stabilizing member comprises another structure, for example, a circumferential ring.

Figure 7C:
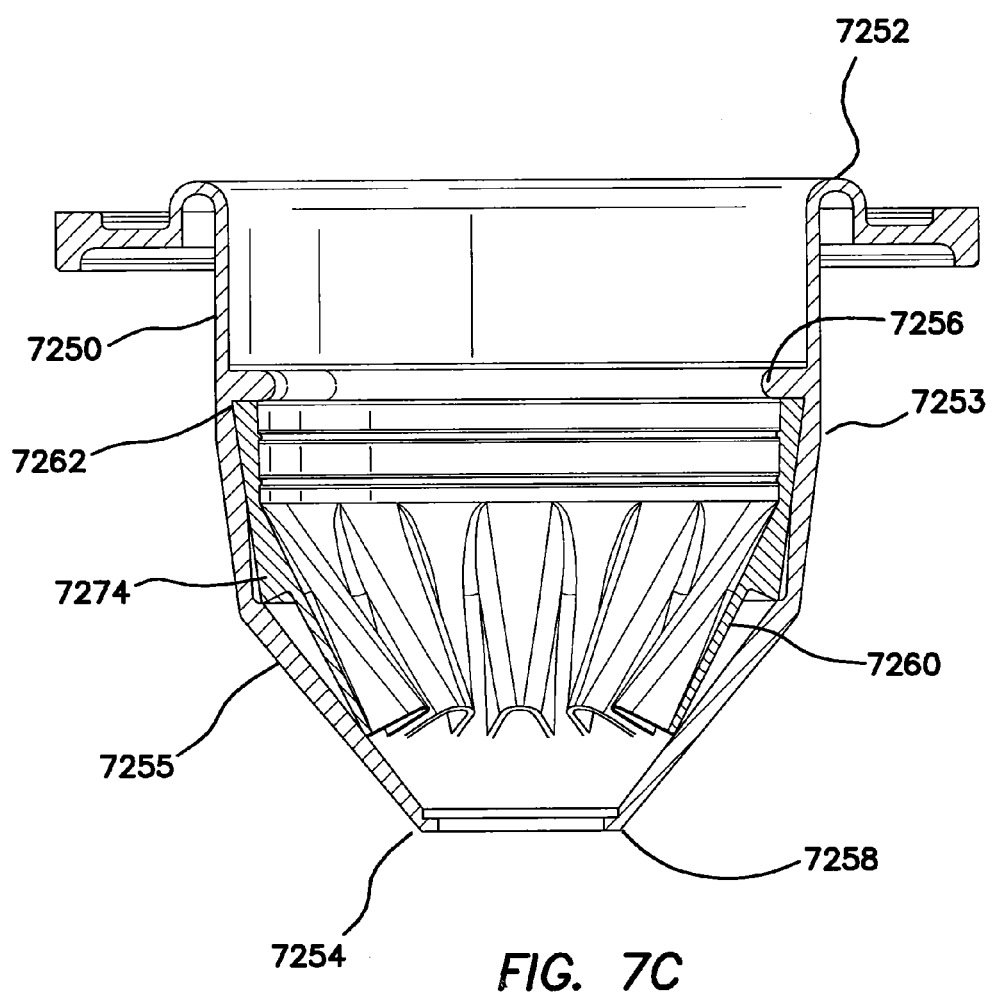
FIG. 7C is a side cross section of the trocar shield mounted in an instrument seal.

FIG. 7C is a side cross section of a subassembly of an access device comprising the trocar shield 7260 and an instrument seal 7250. In the illustrated embodiment, the instrument seal 7250 comprises a septum seal, which is generally similar to the embodiments described above. The instrument seal 7250 is generally tubular, comprising an instrument access channel extending from a proximal end 7252 to a distal end 7254 thereof. The proximal end 7252 comprises a first portion 7253, and the distal end 7254 comprises a second portion 7255. The first portion 7253 is generally cylindrical, conical, or comprises both cylindrical and conical portions. The second portion 7255 is conical, converging distally, and comprises a septum seal 7258 comprising an opening. In some embodiments in which the first portion 7253 comprises a conical portion, the second portion 7255 of the instrument seal 7250 has a greater cone angle than the first portion, that is, converges more rapidly. Consequently, the second portion 7255 is also referred to as a conical portion. A radial flange or lip 7256 extends inwardly from the first portion 7253.

As illustrated in FIG. 7C, the trocar shield 7260 is captured between the flange 7256 and the conical portion 7255 of the instrument seal 7250, with the proximal end 7262 of the trocar shield contacting the flange 7256, and the distal end 7254 of the trocar shield contacting the conical portion 7255. Consequently, the trocar shield 7260 is mounted on or carried on the instrument seal 7250. The fins 7274 contact the inner surface of the first portion 7253 of the instrument seal, creating additional contact points between the trocar shield 7260 and the instrument seal 7250 compared, for example, with the embodiment illustrated in FIG. 4A. The additional contact points created by the fins 7274 stabilize and/or retain the trocar shield 7260 within the instrument seal 7250 compared with the embodiment illustrated in FIG. 4A. In the illustrated embodiment, the fins 7274 extend to the boundary between the first portion 7253 and the second portion 7255 of the instrument seal. In other embodiments, the fins 7274 have a different height, for example, shorter and/or taller.

For example, in some cases, off-axis contact of an instrument with the trocar shield 4260 illustrated in FIG. 4A rotates the trocar shield 4260 around a transverse axis relative to the instrument seal 4250, tipping one side of the proximal end 4262 upward and an opposite side downward, thereby misaligning the opening 4270 of the trocar shield 4260 from the opening at the distal end 4254 of the instrument seal 4250. The fins 7274 improve retention of the trocar shield 7260 illustrated in FIG. 7C, thereby resisting transverse rotation of the trocar shield 7260 relative to the instrument seal 7250.

In some embodiments, withdrawing an instrument from the seal assembly 4200 illustrated in FIG. 4A dislodges the trocar shield 4260 from the instrument seal 4250, popping the trocar shield 4260 completely or partially from the flange 4256. The additional contact from the fins 7274 of the embodiment illustrated in FIG. 7C resist forces dislodging the trocar shield 7260 from the instrument seal 7250.

Figure 8A:
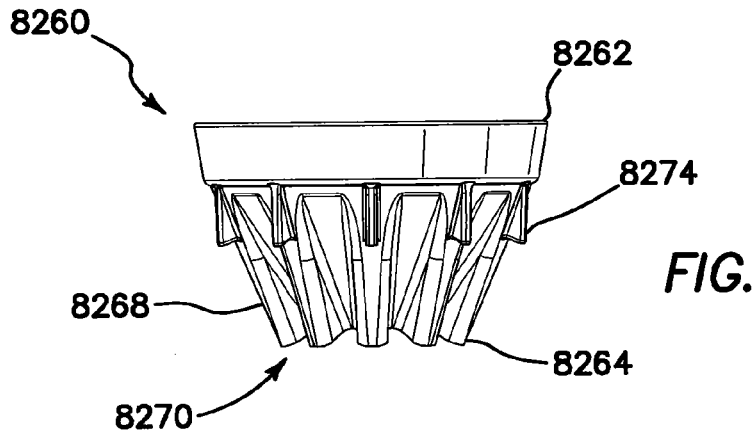
FIGS. 8A, 8B, and 8C are side, top, and side cross-sectional views of another embodiment of a trocar shield.
Figure 8B:
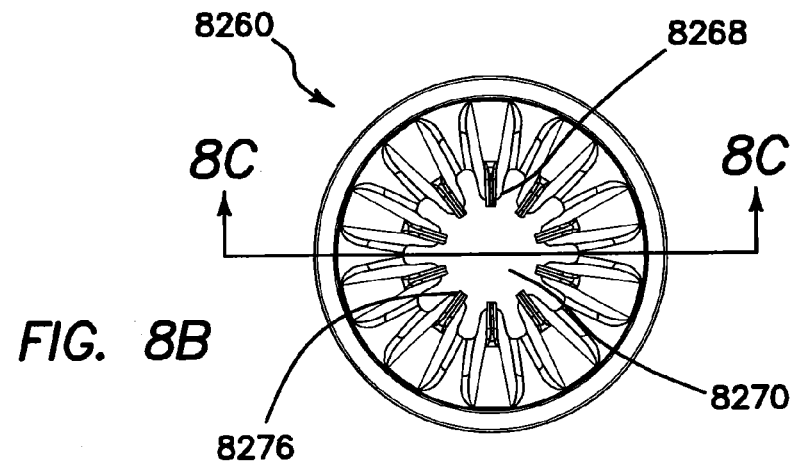
Figure 8C:
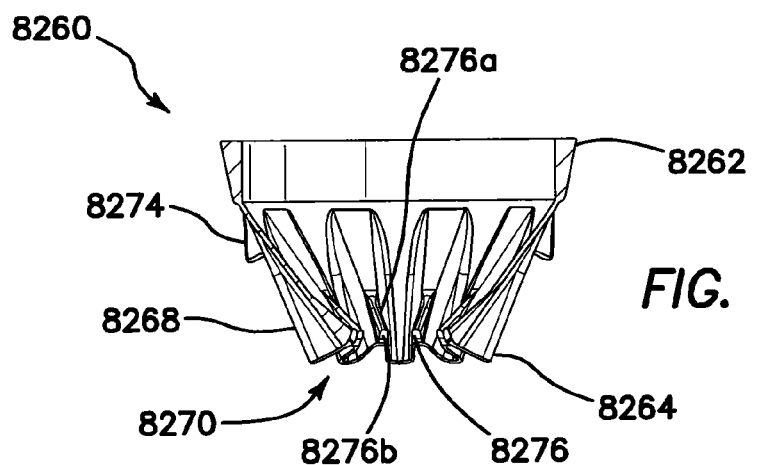

FIGS. 8A, 8B, and 8C are side, top, and side cross-sectional views of another embodiment of a trocar shield 8260 that is generally similar to the embodiments described above, and that is useful in the access devices discussed above. The trocar shield 8260 is generally frustoconical, comprising a wider proximal end 8262 and a narrower distal end 8264. A plurality of radial pleats 8268 extend proximally from the distal end 8264, defining an opening 8270 at the distal end 8264. A plurality of radially extending fins 8274 alternate with the pleats 8268, and are disposed near the proximal ends thereof.

A cam 8276, best viewed in FIGS. 8B and 8C, is disposed at the distal end of each pleat 8268 on the interior surface of the trocar shield 8260, extending into the instrument channel. Consequently, in the illustrated embodiment, the cams 8276 define a minimum diameter of the opening 8270. Some embodiments comprise fewer cams 8276. In the illustrated embodiment, each cam 8276 is generally triangular or pie-shaped, with a longer proximal surface 8276a and a shorter distal surface 8276b. In the illustrated embodiment, distal ends of the cams 8276 are substantially coincident with distal ends of the pleats 8286. In other embodiments, at least one cam 8276 extends distally of the associated pleat 8286, or does not extend as far as the associated pleat 8286. In the illustrated embodiment, the proximal surface 8276a is generally straight, while the distal surface 8276b is generally straight and/or convex (radiused). The distal surfaces 8276b together define an exit funnel that reduces drag and/or instrument hang ups on withdrawing instruments therethrough. The proximal surfaces 8276a define an entry funnel.

Other embodiments of the trocar shield do not comprise fins. In other embodiments, the cams are disposed on a trocar shield comprising tangential pleats.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical access device comprising:
   a seal housing comprising a proximal end and a distal end;
   an instrument seal comprising a proximal end, a distal end, and an opening, the instrument seal is disposed in the housing, the instrument seal sealing against an instrument operatively extending through the seal opening; and
   a seal shield mounted with the instrument seal to direct an instrument operatively inserted towards and in contact with the seal opening, the seal shield comprising:
   a distal end converging to a shield opening;
   a plurality of pleats extending proximally from the shield opening, the plurality of pleats comprises a non-elastomeric material and unfolding the plurality of pleats expands the opening of the seal shield, and
   at least one cam disposed at the shield opening of the distal end of the seal shield to direct an instrument operatively withdrawn away from the seal shield, the at least one cam having a straight proximal surface and a curved distal surface.

2. The surgical access device of claim 1 wherein the at least one cam has a proximal surface and a distal surface shorter than the proximal surface.

3. The surgical access device of claim 1 wherein the housing further comprises a cap closing the proximal end thereof and the cap comprises a funnel-shaped entryway having a distal end contacting the seal shield.

4. The surgical access device of claim 1 wherein the proximal end of the instrument seal comprises a tubular first portion, the distal end of the instrument seal comprises a conical second portion that converges to the opening of the instrument seal, and the distal end of the seal shield is disposed in direct contact with the conical second portion of the instrument seal.

5. A surgical access device comprising:
   a seal housing comprising a proximal end and a distal end;
   an instrument seal comprising a proximal end, a distal end, and an opening, the instrument seal is disposed in the housing, the instrument seal sealing against an instrument operatively extending through the seal opening; and
   a seal shield mounted with the instrument seal to direct an instrument operatively inserted towards and in contact with the seal opening, the seal shield comprising:
   a distal end converging to a shield opening;

a plurality of pleats extending proximally from the shield opening, the plurality of pleats comprises a non-elastomeric material and unfolding the plurality of pleats expands the opening of the seal shield, and at least one cam disposed at the shield opening of the distal end of the seal shield to direct an instrument operatively withdrawn away from the seal shield;

wherein the seal shield further comprises a plurality of fins radially extending from the seal shield and in a contacting relationship with the instrument seal.

6. The surgical access device of claim 1 wherein the seal shield comprises a radial flange extending laterally from the seal shield and into the instrument seal.

7. The surgical access device of claim 1 wherein the instrument seal comprises a radial flange extending laterally from the instrument seal and into the seal shield.

8. The surgical access device of claim 1 wherein the seal assembly further comprises a zero seal.

9. The surgical access device of claim 8 wherein the instrument seal further comprises bellows radially extending from the proximal end of the instrument seal fixing the instrument seal to the seal housing.

10. A surgical access device comprising:
a cannula comprising a proximal end, a distal end and a longitudinal axis defining an access channel through the cannula from the proximal end to the distal end thereof; and
a seal assembly disposed at the proximal end of the cannula, comprising:
a zero seal sealing the access channel in the absence of an instrument extending therethrough;
an instrument seal with a seal opening sealing against an instrument operatively inserted therethrough; and
a trocar shield disposed before the instrument and zero seals in the seal assembly, the trocar shield comprises:
a proximal end,
a distal end comprising a plurality of longitudinal pleats converging to a shield opening at the distal end of the trocar shield to lead an instrument operatively inserted towards and in contact with the seal opening, and
at least one cam disposed near the shield opening at the distal end of the trocar shield to lead an instrument operatively withdrawn away from the shield opening;
wherein the at least one cam has a straight proximal surface and a curved distal surface.

11. The surgical access device of claim 10 wherein the at least one cam is disposed on at least one of the plurality of longitudinal pleats.

12. The surgical access device of claim 10 further comprising a cap securing the zero seal, the instrument seal, and the trocar shield in a seal housing, wherein the access channel extends through the cap, and wherein a distal end of the cap extends into and contacts the trocar shield.

13. A surgical access device comprising:
a cannula comprising a proximal end, a distal end and a longitudinal axis defining an access channel through the cannula from the proximal end to the distal end thereof; and
a seal assembly disposed at the proximal end of the cannula, comprising:
a zero seal sealing the access channel in the absence of an instrument extending therethrough;
an instrument seal with a seal opening sealing against an instrument operatively inserted therethrough; and
a trocar shield disposed before the instrument and zero seals in the seal assembles the trocar shield comprises:
a proximal end,
a distal end comprising a plurality of longitudinal pleats converging to a shield opening at the distal end of the trocar shield to lead an instrument operatively inserted towards and in contact with the seal opening, and
at least one cam disposed near the shield opening at the distal end of the trocar shield to lead an instrument operatively withdrawn away from the shield opening;
wherein the trocar shield comprises a plurality of stabilizing fins radially extending from the trocar shield and in a contacting relationship with the instrument seal.

14. The surgical access device of claim 10 wherein the seal shield comprises a radial flange extending laterally from the seal shield and into the instrument seal.

15. The surgical access device of claim 14 wherein the instrument seal comprises a groove that engages the radial flange.

16. The surgical access device of claim 10 wherein a smallest diameter of the opening of the trocar shield is larger than the diameter of the opening of the instrument seal.

* * * * *